United States Patent
Krivopisk et al.

(10) Patent No.: US 10,064,541 B2
(45) Date of Patent: Sep. 4, 2018

(54) ENDOSCOPE CONNECTOR COVER DETECTION AND WARNING SYSTEM

(71) Applicant: EndoChoice Inc., Alpharetta, GA (US)

(72) Inventors: Leonid Krivopisk, Nesher (IL); Yuri Gershov, Haifa (IL)

(73) Assignee: EndoChoice, Inc., Alpharetta, GA (US)

( * ) Notice: Subject to any disclaimer, the term of this patent is extended or adjusted under 35 U.S.C. 154(b) by 585 days.

(21) Appl. No.: 14/457,268

(22) Filed: Aug. 12, 2014

(65) Prior Publication Data
US 2015/0045614 A1  Feb. 12, 2015

Related U.S. Application Data

(60) Provisional application No. 61/865,078, filed on Aug. 12, 2013.

(51) Int. Cl.
| | | |
|---|---|---|
| *A61B 1/06* | (2006.01) | |
| *A61B 1/04* | (2006.01) | |
| *A61B 1/00* | (2006.01) | |
| *A61B 1/12* | (2006.01) | |

(52) U.S. Cl.
CPC ...... *A61B 1/00121* (2013.01); *A61B 1/00055* (2013.01); *A61B 1/00057* (2013.01); *A61B 1/00137* (2013.01); *A61B 1/121* (2013.01)

(58) Field of Classification Search
CPC ... A61B 1/00; A61B 1/00112; A61B 1/00121; A61B 1/00124; A61B 1/00059; A61B 1/121; A61B 1/00137; A61B 1/00055; A61M 16/0051; A61M 2205/14
USPC ........ 600/109, 132, 134, 160, 103, 117, 118
See application file for complete search history.

(56) References Cited

U.S. PATENT DOCUMENTS

| | | |
|---|---|---|
| 3,639,714 A | 2/1972 | Fujimoto |
| 3,955,064 A | 5/1976 | Demetrio |
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |

(Continued)

FOREIGN PATENT DOCUMENTS

| | | |
|---|---|---|
| CA | 2297986 | 3/1999 |
| CA | 2765559 | 12/2010 |

(Continued)

OTHER PUBLICATIONS

International Search Report for PCT/US14/37004, dated Sep. 25, 2014.

(Continued)

*Primary Examiner* — John P Leubecker
*Assistant Examiner* — William Chou
(74) *Attorney, Agent, or Firm* — Bookoff McAndrews, PLLC

(57) ABSTRACT

In an embodiment, the present specification is an alarm/warning system for notifying a user cleaning an endoscope that the main connector/electrical connector of endoscope has not been covered by a connector cover. The warning system indicates an absence of a connector cover cup when the connector of the endoscope is not connected to a main control unit.

30 Claims, 20 Drawing Sheets

(56) References Cited

U.S. PATENT DOCUMENTS

| | | | |
|---|---|---|---|
| 4,588,294 A | 5/1986 | Siegmund | |
| 4,641,635 A | 2/1987 | Yabe | |
| 4,727,859 A | 3/1988 | Lia | |
| 4,764,001 A | 8/1988 | Yokota | |
| 4,801,792 A | 1/1989 | Yamasita | |
| 4,825,850 A | 5/1989 | Opie | |
| 4,877,314 A | 10/1989 | Kanamori | |
| 4,902,115 A | 2/1990 | Takahashi | |
| 4,976,522 A | 12/1990 | Igarashi | |
| 4,984,878 A | 1/1991 | Miyano | |
| 5,007,406 A | 4/1991 | Takahashi | |
| 5,014,685 A | 5/1991 | Takahashi | |
| 5,154,707 A * | 10/1992 | Rink | A61B 18/20 128/898 |
| 5,193,525 A | 3/1993 | Silverstein | |
| 5,224,929 A | 7/1993 | Remiszewski | |
| 5,296,971 A | 3/1994 | Mori | |
| 5,359,456 A | 10/1994 | Kikuchi | |
| 5,395,329 A | 3/1995 | Fleischhacker | |
| 5,447,148 A | 9/1995 | Oneda | |
| 5,460,167 A | 10/1995 | Yabe | |
| 5,464,007 A | 11/1995 | Krauter | |
| 5,475,420 A | 12/1995 | Buchin | |
| 5,489,256 A | 2/1996 | Adair | |
| 5,518,501 A | 5/1996 | Oneda | |
| 5,518,502 A | 5/1996 | Kaplan | |
| 5,547,455 A | 8/1996 | McKenna | |
| 5,547,457 A | 8/1996 | Tsuyuki | |
| 5,575,755 A | 11/1996 | Krauter | |
| 5,587,839 A | 12/1996 | Miyano | |
| 5,630,782 A | 5/1997 | Adair | |
| 5,630,798 A | 5/1997 | Beiser | |
| 5,662,588 A | 9/1997 | Iida | |
| 5,674,182 A | 10/1997 | Suzuki | |
| 5,685,821 A | 11/1997 | Pike | |
| 5,685,823 A | 11/1997 | Ito | |
| 5,702,347 A | 12/1997 | Yabe | |
| 5,707,344 A | 1/1998 | Nakazawa | |
| 5,725,474 A | 3/1998 | Yasui | |
| 5,725,476 A | 3/1998 | Yasui | |
| 5,725,477 A | 3/1998 | Yasui | |
| 5,725,478 A | 3/1998 | Saad | |
| 5,777,797 A | 7/1998 | Miyano | |
| 5,782,751 A | 7/1998 | Matsuno | |
| 5,800,341 A | 9/1998 | McKenna | |
| 5,810,715 A | 9/1998 | Moriyama | |
| 5,810,717 A | 9/1998 | Maeda | |
| 5,810,770 A | 9/1998 | Chin | |
| 5,830,121 A | 11/1998 | Enomoto | |
| 5,836,894 A | 11/1998 | Sarvazyan | |
| 5,860,913 A | 1/1999 | Yamaya | |
| 5,870,234 A | 2/1999 | Ebbesmeier nee Schitthof | |
| 5,916,148 A | 6/1999 | Tsuyuki | |
| 5,940,126 A | 8/1999 | Kimura | |
| 6,058,109 A | 5/2000 | Lechleider | |
| 6,095,970 A | 8/2000 | Hidaka | |
| 6,095,971 A | 8/2000 | Takahashi | |
| 6,117,068 A | 9/2000 | Gourley | |
| 6,181,481 B1 | 1/2001 | Yamamoto | |
| 6,196,967 B1 | 3/2001 | Lim | |
| 6,261,226 B1 | 7/2001 | McKenna | |
| 6,277,064 B1 | 8/2001 | Yoon | |
| 6,359,674 B1 | 3/2002 | Horiuchi | |
| 6,375,610 B2 | 4/2002 | Verschuur | |
| 6,402,738 B1 | 6/2002 | Ouchi | |
| 6,419,626 B1 | 7/2002 | Yoon | |
| 6,476,851 B1 | 11/2002 | Nakamura | |
| 6,636,254 B1 | 10/2003 | Onishi | |
| 6,638,214 B2 | 10/2003 | Akiba | |
| 6,673,012 B2 | 1/2004 | Fujii | |
| 6,690,337 B1 | 2/2004 | Mayer, III | |
| 6,712,760 B2 | 3/2004 | Sano | |
| 6,832,984 B2 | 12/2004 | Stelzer | |
| 6,888,119 B2 | 5/2005 | Iizuka | |
| 7,154,378 B1 | 12/2006 | Ertas | |
| 7,435,218 B2 | 10/2008 | Krattiger | |
| 7,621,869 B2 | 11/2009 | Ratnakar | |
| 7,630,148 B1 | 12/2009 | Yang | |
| 7,701,650 B2 | 4/2010 | Lin | |
| 7,713,246 B2 | 5/2010 | Shia | |
| 7,746,572 B2 | 6/2010 | Asami | |
| 7,813,047 B2 | 10/2010 | Wang | |
| 7,828,725 B2 | 11/2010 | Maruyama | |
| 7,918,788 B2 | 4/2011 | Lin | |
| 7,927,272 B2 | 4/2011 | Bayer | |
| 7,967,745 B2 | 6/2011 | Gilad | |
| 7,976,462 B2 | 7/2011 | Wright | |
| 8,064,666 B2 | 11/2011 | Bayer | |
| 8,182,422 B2 | 5/2012 | Bayer | |
| 8,197,399 B2 | 6/2012 | Bayer | |
| 8,235,887 B2 | 8/2012 | Bayer | |
| 8,262,558 B2 | 9/2012 | Sato | |
| 8,287,446 B2 | 10/2012 | Bayer | |
| 8,289,381 B2 | 10/2012 | Bayer | |
| 8,300,325 B2 | 10/2012 | Katahira | |
| 8,310,530 B2 | 11/2012 | Bayer | |
| 8,353,860 B2 | 1/2013 | Boulais | |
| 8,447,132 B1 | 5/2013 | Galil | |
| 8,449,457 B2 | 5/2013 | Aizenfeld | |
| 8,460,182 B2 | 6/2013 | Ouyang | |
| 8,585,584 B2 | 11/2013 | Ratnakar | |
| 8,587,645 B2 | 11/2013 | Bayer | |
| 8,672,836 B2 | 3/2014 | Higgins | |
| 8,715,168 B2 | 5/2014 | Ratnakar | |
| 8,797,392 B2 | 8/2014 | Bayer | |
| 8,872,906 B2 | 10/2014 | Bayer | |
| 8,926,502 B2 | 1/2015 | Levy | |
| 9,044,185 B2 | 6/2015 | Bayer | |
| 9,101,266 B2 | 8/2015 | Levi | |
| 9,101,268 B2 | 8/2015 | Levy | |
| 9,101,287 B2 | 8/2015 | Levy | |
| 9,289,110 B2 | 3/2016 | Woolford | |
| 9,314,147 B2 | 4/2016 | Levy | |
| 9,320,419 B2 | 4/2016 | Kirma | |
| 2001/0036322 A1 | 11/2001 | Bloomfield | |
| 2002/0017515 A1 | 2/2002 | Obata | |
| 2002/0047897 A1 | 4/2002 | Sugimoto | |
| 2002/0087047 A1 | 7/2002 | Remijan | |
| 2002/0109771 A1 | 8/2002 | Ledbetter | |
| 2002/0109774 A1 | 8/2002 | Meron | |
| 2002/0161279 A1 | 10/2002 | Luloh | |
| 2002/0161281 A1 | 10/2002 | Jaffe | |
| 2002/0172498 A1 | 11/2002 | Esenyan | |
| 2002/0183591 A1 | 12/2002 | Matsuura | |
| 2003/0030918 A1 | 2/2003 | Murayama | |
| 2003/0063398 A1 | 4/2003 | Abe | |
| 2003/0076411 A1 | 4/2003 | Iida | |
| 2003/0083552 A1 | 5/2003 | Remijan | |
| 2003/0128893 A1 | 7/2003 | Castorina | |
| 2003/0139650 A1 | 7/2003 | Homma | |
| 2003/0153897 A1 | 8/2003 | Russo | |
| 2003/0158503 A1 | 8/2003 | Matsumoto | |
| 2004/0015054 A1 | 1/2004 | Hino | |
| 2004/0046865 A1 | 3/2004 | Ueno | |
| 2004/0061780 A1 | 4/2004 | Huffman | |
| 2004/0064019 A1* | 4/2004 | Chang | A61B 1/00059 600/180 |
| 2004/0077927 A1 | 4/2004 | Ouchi | |
| 2004/0106850 A1 | 6/2004 | Yamaya | |
| 2004/0133072 A1 | 7/2004 | Kennedy | |
| 2004/0138532 A1 | 7/2004 | Glukhovsky | |
| 2004/0158129 A1 | 8/2004 | Okada | |
| 2004/0160682 A1 | 8/2004 | Miyano | |
| 2004/0190159 A1 | 9/2004 | Hasegawa | |
| 2004/0249247 A1 | 12/2004 | Iddan | |
| 2004/0260151 A1 | 12/2004 | Akiba | |
| 2005/0018042 A1 | 1/2005 | Rovegno | |
| 2005/0020876 A1 | 1/2005 | Shioda | |
| 2005/0038317 A1 | 2/2005 | Ratnakar | |
| 2005/0047134 A1 | 3/2005 | Mueller | |
| 2005/0057687 A1 | 3/2005 | Irani | |
| 2005/0090709 A1 | 4/2005 | Okada | |
| 2005/0096501 A1 | 5/2005 | Stelzer | |
| 2005/0119527 A1 | 6/2005 | Banik | |

(56) References Cited

U.S. PATENT DOCUMENTS

| | | |
|---|---|---|
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0062814 A1* | 3/2009 | Omori ................... A61B 34/71 606/130 |
| 2009/0076327 A1* | 3/2009 | Ohki ................. A61B 1/00124 600/127 |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1* | 10/2011 | Yoshino ............. A61B 1/00009 348/65 |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |

(56) References Cited

U.S. PATENT DOCUMENTS

| | | |
|---|---|---|
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |

(56) References Cited

FOREIGN PATENT DOCUMENTS

| | | |
|---|---|---|
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 A1 | 12/2010 |
| WO | 2012038958 | 3/2012 |
| WO | 2012056453 A2 | 5/2012 |
| WO | 2012075153 A2 | 6/2012 |
| WO | 2012077116 | 6/2012 |
| WO | 2012077117 A1 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action dated Feb. 26, 2016 for U.S. Appl. No. 14/274,323.
Office Action dated Feb. 4, 2016 for U.S. Appl. No. 14/271,234.
Notice of Allowance dated Mar. 29, 2016 for U.S. Appl. No. 13/680,646.
Corrected Notice of Allowance dated Apr. 13, 2016 for U.S. Appl. No. 13/680,646.
Office Action dated Mar. 24, 2016 for U.S. Appl. No. 13/212,627.
Office Action dated Mar. 28, 2016 for U.S. Appl. No. 13/119,032.
Notice of Allowance dated Mar. 28, 2016 for U.S. Appl. No. 13/413,059.
Office Action dated Mar. 23, 2016 for U.S. Appl. No. 13/713,449.
Office Action dated May 6, 2016 for U.S. Appl. No. 14/263,896.
Office Action dated May 25, 2016 for U.S. Appl. No. 14/271,234.
Office Action dated May 5, 2016 for U.S. Appl. No. 14/278,338.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.

(56) References Cited

OTHER PUBLICATIONS

Notice of Allowance dated Apr. 18, 2017 for U.S. Appl. No. 13/713,449.
Office Action dated Apr. 19, 2017 for U.S. Appl. No. 14/988,551.

* cited by examiner

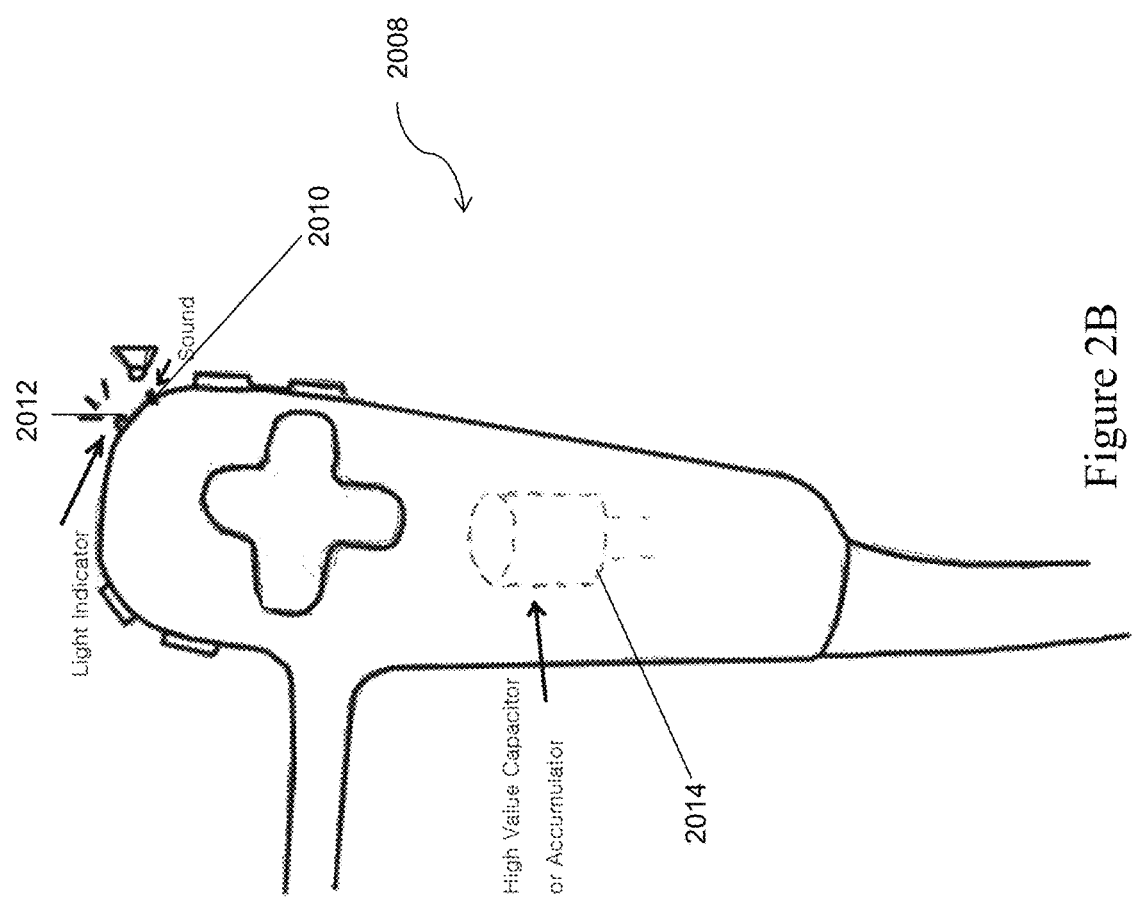

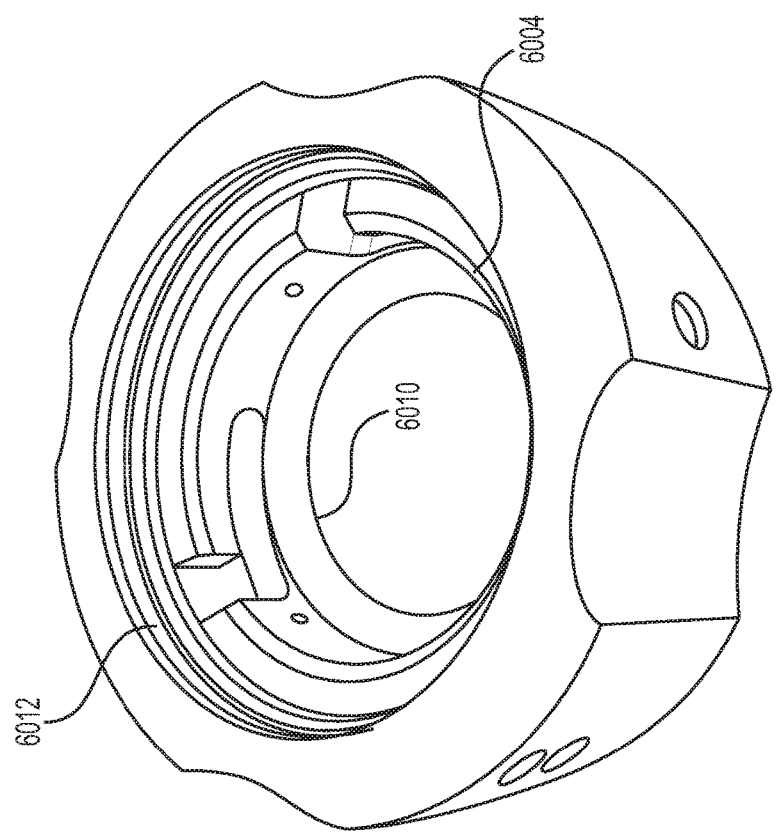

ENDOSCOPE CONNECTOR COVER DETECTION AND WARNING SYSTEM

CROSS-REFERENCE TO RELATED APPLICATIONS

The present application relies on, for priority, U.S. Provisional Patent Application No. 61/865,078, entitled "Connector Cover Detection and Warning System", and filed on Aug. 12, 2013, which is herein incorporated by reference in its entirety.

FIELD

The present specification generally relates to an endoscope and more specifically to a warning system for indicating an absence of a connector cover cup on a main connector/electrical connector of the endoscope.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Endoscopes, such as colonoscopes, that are currently being used, typically have a front camera for viewing the internal organ, such as the colon, an illuminator, a fluid injector for cleaning the camera lens and other portions of the endoscope, a working channel for insertion of surgical tools, for example, tools for removing polyps found in the colon. Often, endoscopes also have fluid injectors ("jet") for cleaning a body cavity, such as the colon, into which they are inserted.

Endoscopes such as but not limited to colono/gastroscopes are washed after every use. The endoscopes are connected to a main control unit via a main connector of the endoscope apparatus that also comprises an electrical connector to establish electrical communication between the endoscope apparatus and the main control unit.

While washing the endoscopes with water or other cleaning fluids, it is important to seal off the electrical connector by using a cap or any other means, in order to prevent the washing liquid from entering the connector and causing damage to electrical components. It is possible that sometimes medical professionals cleaning the endoscope may forget to put a connector cover cup on the electrical connector before commencing the washing, resulting in damage to the connector caused by water and other harsh cleaning chemicals.

Hence, there is a need in the art for an alarm/warning system which could detect the absence of a connector cover cup and accordingly notify a medical professional cleaning an endoscope that the electrical connector has not been covered by a connector cover cup. There is thus a need for a warning system which indicates an absence of a connector cover cup when the main connector is not connected to a main control unit.

SUMMARY

The following embodiments and aspects thereof are described and illustrated in conjunction with systems, tools and methods, which are meant to be exemplary and illustrative, not limiting in scope.

In an embodiment, the present specification describes an endoscope assembly comprising a connector for connecting the endoscope assembly to a control unit of endoscope, and a warning system for indicating an absence of a connector cover adapted to cover said connector when said connector is not connected to the control unit, the warning system comprising: an alarm unit; a power source for powering the alarm unit; and a detection system for detecting an absence of the connector cover and activating the alarm unit if the connector cover is absent.

Optionally, the alarm unit comprises a light emitting diode. Optionally, the alarm unit comprises a sound producing speaker.

Optionally, the warning system is installed in the connector.

Optionally, the alarm unit of said warning system is installed in the handle portion of the endoscope.

In some embodiments, the power supply for powering the alarm unit may comprise a high capacitance capacitor. In some embodiments, the power supply for powering the alarm unit may comprise an electrical accumulator.

In some embodiments, the power source for powering the alarm unit is charged when the connector is connected to the main control unit.

Optionally, the detection system comprises a microswitch for detecting an absence of the connector cover.

Optionally, the detection system comprises a reed contact with magnetic system for detecting an absence of the connector cover.

Optionally, the detection system comprises a photodiode or phototransistor for detecting an absence of the connector cover. In some embodiments, the endoscope assembly may further comprise a comparator to compare a signal generated by the photodiode with a threshold signal to estimate a presence or absence of said connector cover.

Optionally, the detection system comprises an optocoupler for detecting an absence of the connector cover.

In another embodiment, the present specification describes an endoscope system, including an endoscope assembly and control unit, comprising: a connector for connecting the endoscope assembly to the control unit; a detection system to generate a signal indicative of a presence or absence of a connector cover adapted to cover said connector when said connector is not connected to the control unit; and a notification system to receive and process said signal generated by the detection system and, based on said signal, activate or deactivate an alarm to communicate an absence or presence of said connector cover.

In some embodiments, said notification system comprises a microcontroller or a processing unit to analyze said signal.

Optionally, said notification system is configured as part of said connector of the endoscope system.

Optionally, said notification system is configured as part of a handle portion of the endoscope assembly.

Optionally, said notification system comprises at least one of a light based alarm unit or a sound based alarm unit.

In some embodiments, said detection system is configured as a part of said connector of the endoscope system.

Optionally, said detection system comprises at least one of a micro switch or a reed contact with a magnetic system.

Optionally, said detection system comprises a photodiode. In some embodiments, the endoscope system may further comprise a comparator to compare a signal generated by the photodiode with a threshold signal to estimate a presence or absence of said connector cover.

Optionally, said detection system comprises an optocoupler.

In some embodiments, the endoscope system further comprises a power source for powering said alarm unit. Optionally, the power source is at least one of a capacitor or an electrical accumulator. Optionally, the power source used for powering the alarm unit is adapted to be charged when said connector is connected to the control unit.

In another embodiment, the present specification describes an endoscope system comprising: a connector for connecting the endoscope assembly to a main control unit of endoscope; a connector cover to encompass at least a portion of said connector when said connector is not connected to said main control unit; an alarm system to indicate an absence of said connector cover over said connector; and a main control unit comprising a regulator to control said alarm system when said connector is connected with the main control unit.

In some embodiments, the connector cover comprises a micro switch to detect a presence of the connector cover when said connector is not connected to said main control unit.

In some embodiments, the connector cover comprises a reed contact with a magnetic switch to detect a presence of the connector cover when said connector is not connected to said main control unit. Further, the connector cover may comprise a magnet to regulate a function of said reed contact.

In some embodiments, the connector cover comprises a photo sensing device to detect a presence of the connector cover when said connector is not connected to said main control unit.

In some embodiments, the connector cover comprises an optocoupler to detect a presence of the connector cover when said connector is not connected to said main control unit.

Optionally, the alarm system comprises at least one of an acoustic indicator or a visual indicator.

In some embodiments, the connector comprises at least one of a power supply module to provide a power source for at least a portion of the alarm system, a charger, or a power control unit to regulate a power supply module.

In some embodiments, the main control unit provides power to charge said power supply module when said main control unit is connected to said connector.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 2B illustrates a notification/alarm system integrated within a handle portion of an endoscope apparatus in accordance with an embodiment of the present specification;

DETAILED DESCRIPTION

Figure 1:
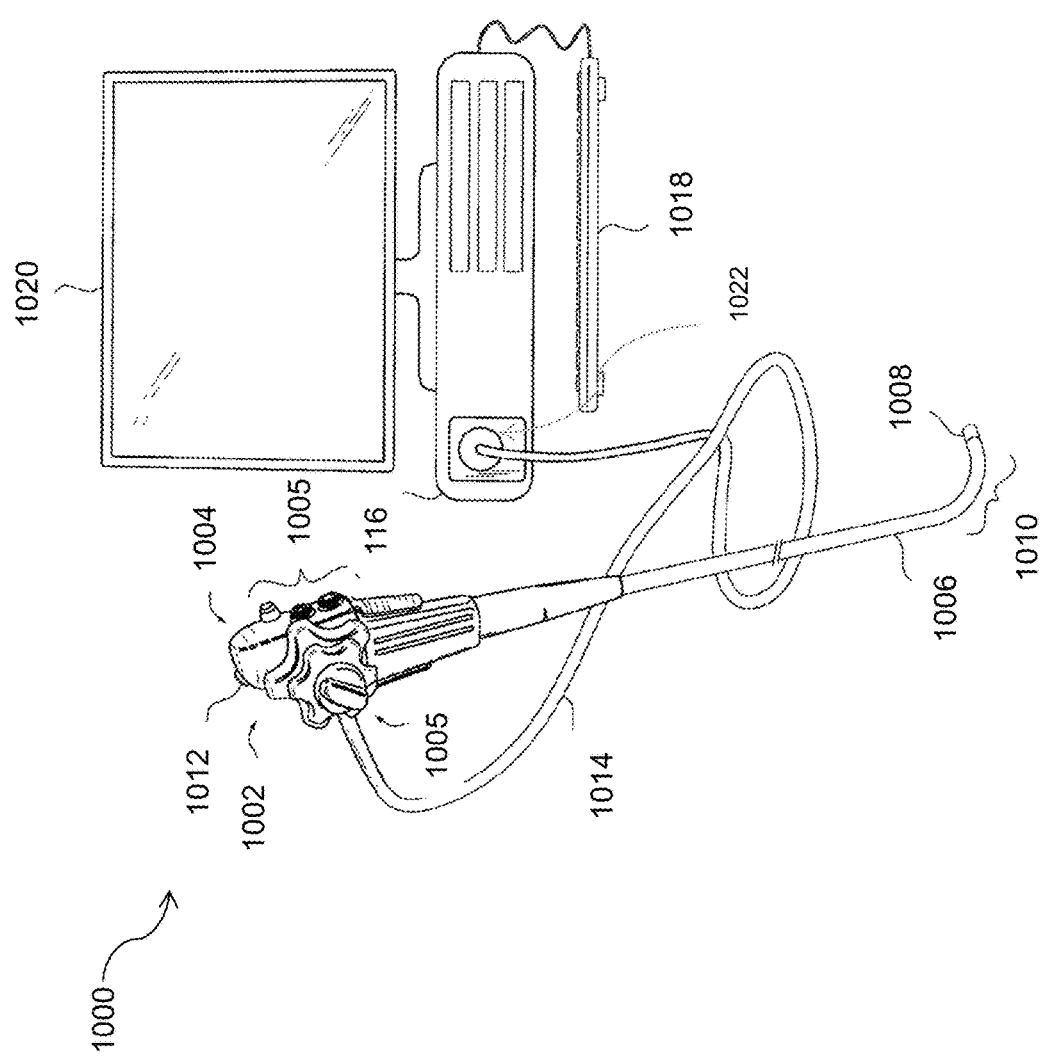
FIG. 1 shows a semi-pictorial view of an exemplary endoscopy system, in accordance with an embodiment of the present specification.

In an embodiment, the present specification describes an alarm/warning system for notifying a user of an endoscope that the electrical connector, which is a part of the main connector of the endoscope, has not been covered by a connector cover cup, which is critical during a cleaning operation. In another embodiment, the warning system indicates an absence of a connector cover cup when the main connector of the endoscope is not connected to the main control unit of an endoscope.

In an embodiment, the warning system described in the present specification comprises a detection system, which detects the absence of the connector cover cup over the electrical connector of the endoscope and subsequently generates a signal indicative of the same to a notification system, which in an embodiment comprises an audible or visual (such as light-based) alarm. On receiving said signal, the notification system notifies the user by triggering an audible and/or visual alarm. In another embodiment, the notification system waits for a specific time interval before trigging the alarm to provide ample time for a user to place the connector cover cup over the electrical connector after detaching the main connector from the main control unit of an endoscope. In another embodiment, the user has the option to manually switch off the alarm to accommodate for situations in which the connector cover cup is misplaced.

In various embodiments, the present specification describes multiple methods and systems to implement the detection and notification systems disclosed herein. However, one of ordinary skill in the art would appreciate that the present specification is not limited in any way by the exact configuration of detection and notification systems.

In an embodiment of the present specification, the alarm/warning system which comprises the detection and notification systems is integrated with the main connector of the endoscopy apparatus. In another embodiment, the alarm/warning system is integrated with the handle portion of the endoscope apparatus. In an embodiment, the detection system employs a micro-switch. In another embodiment, the detection system employs a reed switch. In another embodiment, the detection system employs a photodiode. In yet another embodiment, the detection system employs an optocoupler.

In an embodiment, the notification system comprises an audible sound-based alarm, such as a beeper. In an embodiment, the notification system comprises a visual alarm, such as a light-based alarm. In another embodiment, a light-based sensor comprising one or more LEDs is used as the visual alarm system. In another embodiment, both visual/light and audible/sound based alarm sub-systems are used in the notification system. In another embodiment, a vibration based sensing mechanism is used as the alarm system.

While in an embodiment of the present specification, the connector cover cup is used to cover the entire main connector portion of the endoscope and not just the electrical connector portion, it should be understood by those of ordinary skill in the art that any portion of the main connector may be covered by the connector cover cup of the present specification as long as it achieves the objectives described in the present specification. In an alternate embodiment, the connector cover cup may cover only the electrical connector portion of the main connector of an endoscope. The warning system disclosed in the present specification can be implemented in any of the embodiments having different types of connector cover cups, in accordance with the present specification.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 illustrates an exemplary endoscopy system in which the warning system of the present specification is implemented. The embodiment described in FIG. 1 comprises a multiple viewing elements endoscope, however, it should be apparent to persons of skill in the art, that the warning system of the present specification can be implemented in any type of endoscope system that requires cleaning with fluids after use and that comprises an electrical means such as an electrical connector for connecting the endoscope apparatus with the main control unit. Exemplary endoscopes may be found in U.S. patent application Ser. Nos. 14/229,699; 14/263,896; 14/271,270; 14/273,923; 14/278,293; 14/318,189; 14/317,863; 14/318,249; and Ser. No. 14/278,338, all of which are incorporated herein by reference.

Reference is now made to FIG. 1 which shows a semi-pictorial view of a multiple viewing elements endoscopy system 1000. In an embodiment, the endoscopy system 1000 includes a multiple viewing elements endoscope 1002 which comprises a handle 1004, from which an elongated shaft 1006 emerges and terminates with a tip section 1008, which is turnable by way of a bending section 1010. In an embodiment, the handle 1004 is used for maneuvering elongated shaft 1006 within a body cavity; the handle may include one or more knobs and/or switches 1005 which are used to control bending section 1010 as well as functions such as fluid injection, suction and toggling between multi-viewing elements of tip section 1008. In an embodiment, the handle 1004 further includes one or more working/service channel openings 1012 through which surgical tools are inserted to perform medical procedures on the patient In an embodiment, the tip section 1008 comprises multiple viewing elements and/or optical assemblies. In accordance with an embodiment, the tip section 1008 includes a front viewing element and one or more side viewing elements, whereas according to another embodiment tip section 108 includes only a front viewing element. As shown in FIG. 1, a utility cable 1014 connects the handle 1004 with the main controller 1016. In an embodiment, the utility cable 1014 comprises multiple channels including one or more fluid channels and one or more electrical channels. In an embodiment, the electrical channel(s) includes at least one data cable for transmitting video signals from the front and side-viewing elements to the main controller 1016, as well as at least one power cable for providing electrical power to the viewing elements and to the discrete illuminators located on the tip section 1008. In an embodiment, the utility cable 1014 is coupled to a main connector 1022 which connects the endoscope apparatus to the main controller 1016. In an embodiment, the main connector 1022 comprises an electrical connector which is used to establish both electrical and data communication between the endoscopy apparatus and the main controller 1016.

In an embodiment, the main controller 1016 governs power transmission to the endoscope's tip section 1008, such as for the tip section's viewing elements and illuminators. In another embodiment, the main controller 1016 further controls one or more fluid, liquid and/or suction pumps which supply corresponding functionalities to endoscope 1002. In an embodiment, one or more input devices, such as a keyboard 1018, are connected to main controller 1016 for the purpose of human interaction with the controller. In another configuration (not shown), an input device, such as a keyboard, is integrated with the controller in a same casing.

In an embodiment, a display 1020 is connected to main controller 1016, and is configured to display images and/or video streams received from the viewing elements of the endoscope 1002. In another embodiment, display 1020 is further configured to display a touch interface for allowing a human operator to set various features of system 1000. In another embodiment, display 1020 comprises multiple display panels.

Endoscopes, such as but not limited to colonoscopes and gastroscopes, are washed after every use. Also, endoscopes are usually connected to a main control unit via a main connector as illustrated in FIG. 1. In an embodiment, the warning system of the present specification is implemented in the endoscopy system 1002 such that it causes an alarm to activate to notify a user washing the endoscope without first covering the electrical connector with a connector cover cup. In another embodiment, the present specification comprises a detection means or apparatus integrated in the endoscopy system 1002 which detects the absence of a connector cover cup on the electrical connector and triggers a notification system integrated in the endoscope system 1002.

One of ordinary skill in the art would appreciate that there could be multiple systems and methods for implementing the warning system comprising the detection and notification system of the present specification. Some of these techniques are disclosed in various embodiments of the present specification. However, one of ordinary skill in the art would appreciate that the present invention is not limited in any manner by the configurations of various detection and notification systems disclosed in these embodiments.

In an embodiment, the notification system of the present specification comprises a sound and/or light based alarm system. In another embodiment, the sound and/or light alarm is powered by using an electrical accumulator or a high capacitance capacitor. In an embodiment, the sound and/or light alarm, along with the corresponding power supply, is provided within the electrical connector of the main connector of an endoscope. In another embodiment, the sound and/or light alarm and the corresponding power supply is provided in the handle portion of an endoscope. In an embodiment, the notification system is included with the utility cable 1014. One of ordinary skill in the art would appreciate that there could be multiple ways to position the light and/or sound or any other means of notification system on the endoscope system 1002 without departing from the spirit and scope of present specification. One of ordinary skill in the art would appreciate that the system disclosed in the present specification can also incorporate other types of notification systems apart from sound or light based systems without departing from the spirit and scope. In another embodiment, a vibration based alarm system is used.

Figure 2A:
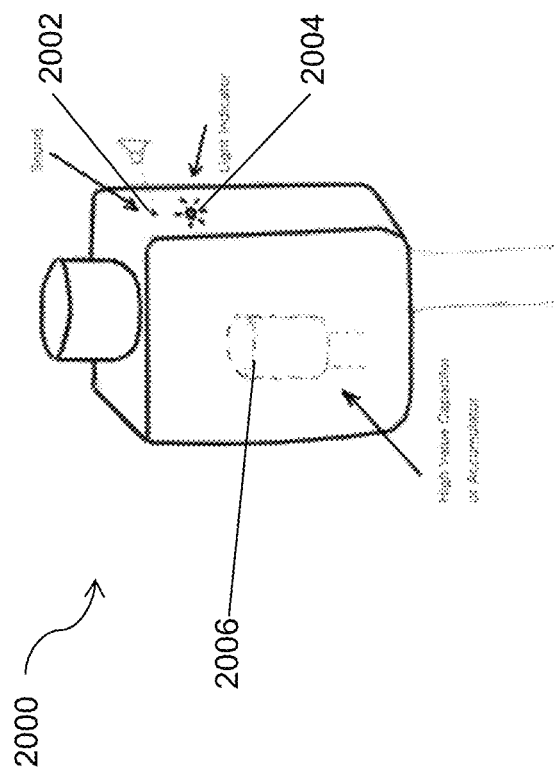
FIG. 2A is an illustration of a notification/alarm system that is integrated with an electrical connector of an endoscope apparatus in accordance with an embodiment of the present specification.

FIG. 2A illustrates a notification system integrated with the electrical connector of the endoscope apparatus in accordance with an embodiment of the present specification. Electrical connector 2000 comprises a speaker 2002 for producing sound and a light source 2004 for emitting light, when the connector cover cup is absent from the electrical connector 2000. A power supply 2006 such as a high capacitance capacitor or an accumulator is also installed within the electrical connector 2000 for powering the speaker 2002 and the light source 2004. In an embodiment, a non-rechargeable battery is used as power supply 2006.

FIG. 2B illustrates a notification system integrated with the handle portion of the endoscope apparatus in accordance with an embodiment of the present specification. Handle 2008 comprises a speaker 2010 for producing a sound and a light source 2012 for emitting light, when a connector cover cup is missing from the electrical connector portion of the endoscope. A power supply 2014 such as a high capacitance capacitor or an accumulator is also installed within the handle 2008 for powering the speaker 2010 and the light source 2012.

In an embodiment, the light sources 2004 and 2012 comprise one or more light emitting diodes (LEDs) that emit light when an absence of connector cover cup is detected. Also, in another embodiment, the power supply unit 2006 and 2014 are charged via the main control unit of the endoscope when the main electrical connector 2000 is connected with the same.

The present specification describes multiple techniques to implement the absent-cap detection system, as disclosed in the present specification. In an embodiment, the absence of a connector cover cup is detected by using a micro-switch. In another embodiment, the absence of a connector cover cup is detected by using a reed contact with a magnetic system. Both embodiments are described below with reference to FIGS. 3A, 3B, 3C, and 3D.

Figure 3A:
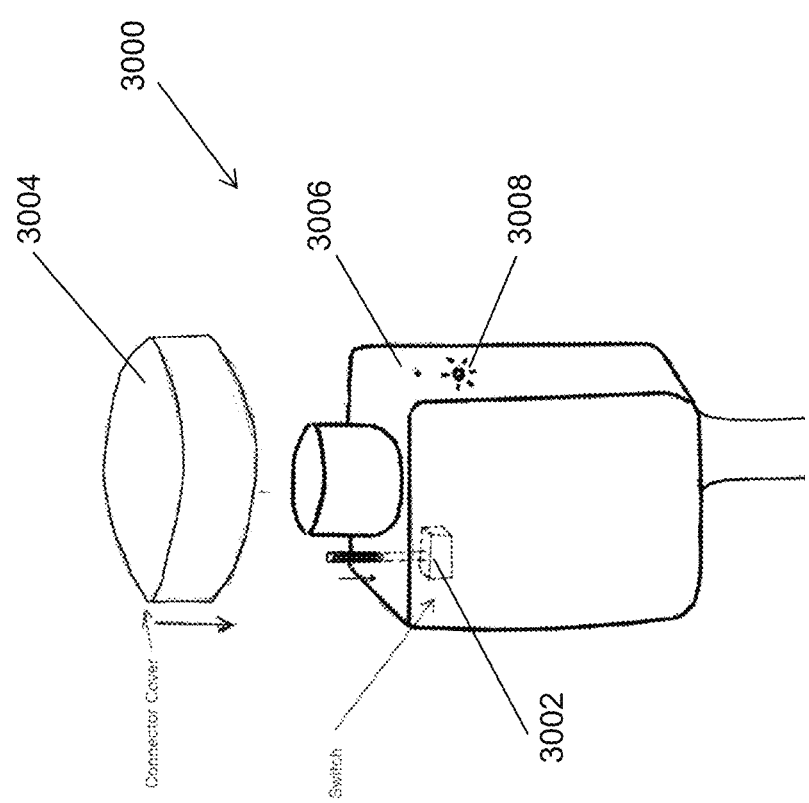
FIG. 3A illustrates an electrical connector comprising a micro-switch for detecting the absence of a connector cover cup, in accordance with an embodiment of the present specification.

FIG. 3A illustrates an electrical connector comprising a micro-switch for detecting the absence of a connector cover cup, in accordance with an embodiment of the present specification. In an embodiment, the endoscope connector 3000 comprises a micro switch 3002 positioned over a top end and a warning system such as a sound alarm 3006 and/or visual alarm/LED 3008. In an embodiment, the connector 3000 further comprises a control logic/unit which is coupled to said warning system and controls its functioning. In an embodiment, a power supply module comprising an accumulator or a high capacitance capacitor is present in the connector 3000 which provides power supply to various components in the connector 3000 such as the control unit and the warning system described above. In an embodiment, the warning system is typically enabled when the main connector is not connected with the main control unit (MCU) and therefore the sound alarm 3006 and/or visual alarm/LED 3008 are in an active state. However, when the MCU is connected with the connector 3000, the MCU regulates the operation of the control unit coupled to the warning system. In an embodiment, the MCU enables a signal indicative of an OFF condition to be transmitted to the control unit coupled to the warning system, which upon receiving said signal, switches off the warning system. In another embodiment, instead of sending a signal indicative of an OFF condition to the control unit, the MCU causes the power supply to the warning system control unit to be disabled which automatically switches off the warning system.

In the above embodiment, when the main connector is detached from the MCU, the warning system is activated. However, in an embodiment, when the connector cover cup 3004 is put on the connector 3000, the micro-switch 3002 is pressed down by the pressure of the connector cover cup 3004, causing a signal indicative of an OFF condition to be transmitted to the warning system control unit, which upon receiving said signal switches off the warning system.

In another embodiment, the micro switch 3002 is configured such that when the connector 3000 is connected with the MCU, the micro switch 3002 is pressed down and it causes a signal indicative of an OFF condition to be transmitted to the control unit coupled to the warning system.

In another embodiment, when the cover cup 3004 is put on the connector 3000, a signal indicative of an OFF condition is transmitted from the micro-switch 3002 to the control unit which also causes the detection system to hibernate in order to minimize power consumption from the power supply module. In an embodiment, the warning system control unit comprises a timer that prevents an alarm occurrence during a predefined time interval when the connector 3000 is disconnected from the main control unit and the connector cover 3004 is put on.

In an embodiment, the connector 3000 comprises a means to manually switch off the warning alarm to provide for the situations wherein the connector cover cap is misplaced by the user.

While in the above embodiment, both a sound-based beeper alarm and a visual-based alarm such as an LED are used to provide the warning signals, in an alternate embodiment the endoscope system may comprise only one such module.

Figure 3B:
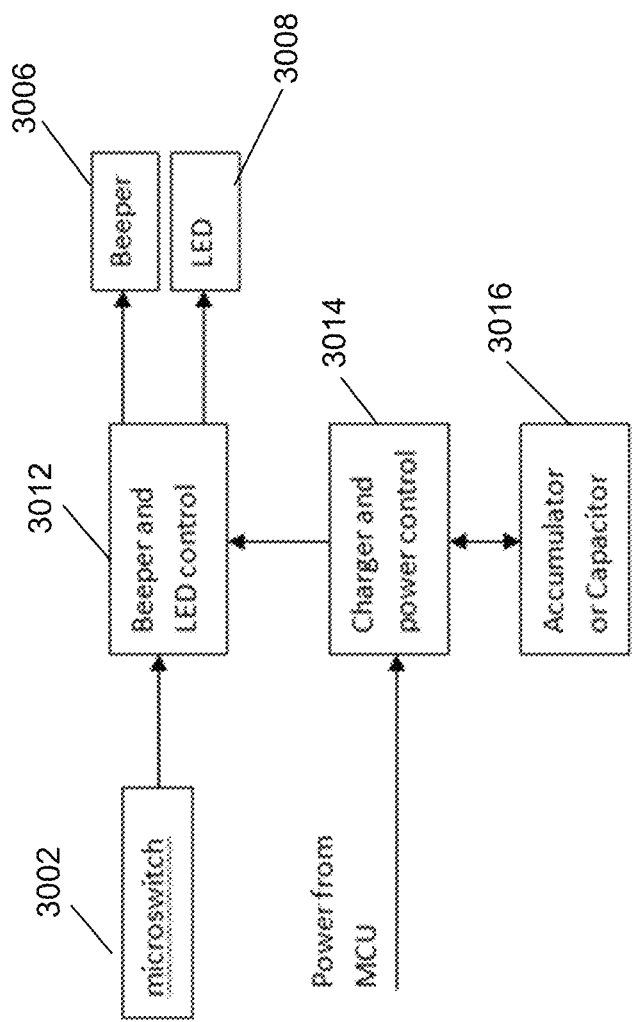
FIG. 3B is a block diagram illustrating the connectivity of components for detecting the absence of a connector cover cup by using a micro-switch, in accordance with an embodiment of the present specification.

FIG. 3B is a block diagram illustrating the connectivity of components for detecting the absence of a connector cover cup by employing a micro-switch, in accordance with an embodiment of the present specification. The micro-switch 3002 is connected to a warning system control unit 3012, for controlling the audio and/or visual alarm which, in turn, is connected to the sound alarm/beeper 3006 and LED 3008. In an embodiment, the endoscope system comprises a charger and power control unit 3014 which is connected to a power supply module 3016 and regulates power to the warning system control unit 3012. In an embodiment, when the main connector is connected with the main control unit (MCU), the power from the MCU charges the power supply module 3016, which comprises an accumulator or a capacitor, via the charger and power control unit 3014. In an embodiment, the charger and power control unit 3014 regulates the current supply to the power supply module 3016 and once the system is fully charged, it disconnects the current supply to the power supply module 3016 to prevent overcharging. In an embodiment, the MCU controls the functioning of warning system control unit 3012 and therefore, controls the warning system comprising sound alarm 3006 and visual alarm/LED 3008. In an embodiment, when the main connector is connected with the MCU, the MCU transmits a signal indicative of an OFF condition to the control unit 3012 through the charger and power control unit 3014. The control unit 3012 receives the signal indicative of an OFF condition and accordingly switches off the warning system comprising alarm 3006 and LED 3008. In other embodiment, the MCU instructs the charger and power control unit 3014 to disable the power to the warning system control unit 3012 causing the warning system to switch off.

In an embodiment, when the main connector is not connected with the MCU, the warning system control unit 3012 is activated and the warning system is switched ON. However, in an embodiment, when the connector cover cup is secured over the main connector, the micro-switch 3002 is pressed down by the pressure of the cover cup, triggering a signal indicative of an OFF condition to the warning system control unit 3012 which, in turn, switches off the warning system.

In another embodiment, the micro-switch 3002 is configured such that when the main connector is connected with the MCU, the connection causes a pressure to be exerted on the micro-switch 3002 similar to the pressure exerted on micro-switch 3002 when it is in contact with the connector cover cup. The pressure from MCU causes the micro-switch 3002 to be pressed down and triggers a signal indicative of an OFF condition to the control unit 3012 which, in turn, switches off the warning system.

Figure 3C:
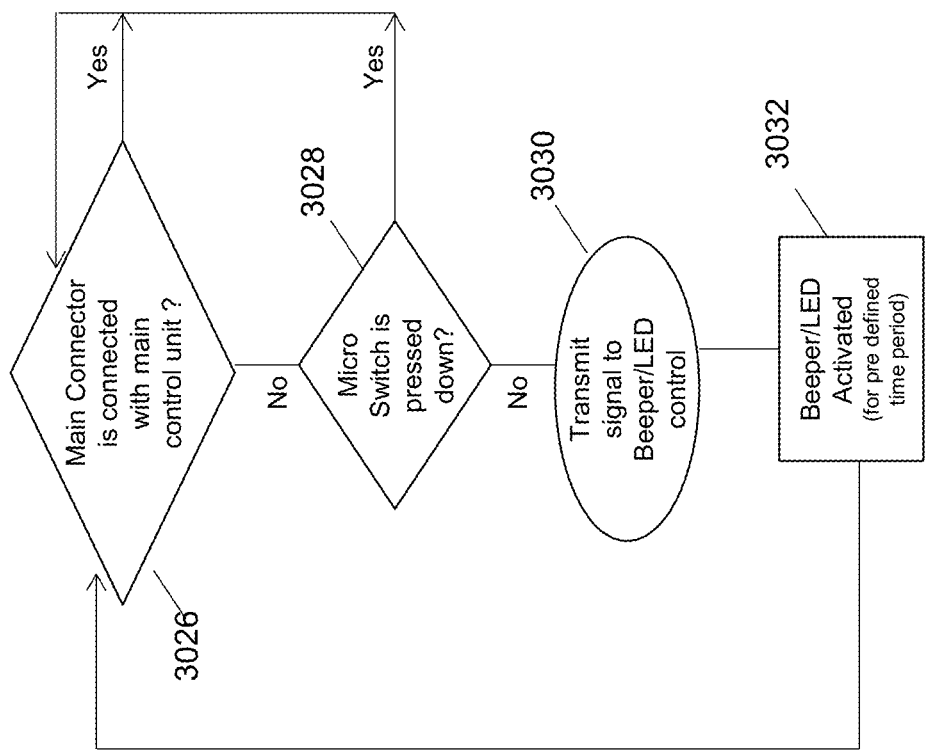
FIG. 3C illustrates a flow chart of the steps implemented by the detection and notification system when employing a micro-switch in accordance with an embodiment of the present specification.

FIG. 3C illustrates a flow chart of the steps implemented by the detection and notification system employing a micro-switch in accordance with an embodiment of the present specification. As shown in FIG. 3C, at step 3026, the detection system checks if the main connector of the endoscope assembly is connected to the main control unit. If the main connector is connected to the main control unit, in an embodiment, the system iteratively checks that this connection is intact. In another embodiment, once it is confirmed that the connection between the main connector and the main control unit is intact, the system iteratively rechecks the connection, beginning at step 3026 after a pre-defined time interval. Thus, in an embodiment, the process is cyclical and this check is performed periodically. In an embodiment, the above check is performed by detecting the status of the power supply coming from the MCU. In an embodiment, the MCU provides the power supply to the endoscope assembly through the charger and power control module 3014 present in the connector 3000 as illustrated in FIG. 3B. In an embodiment, the connector 3000 comprises a means to detect whether the power supply from MCU is ON or OFF. In case the power supply is ON, the system assumes that the connection between connector and MCU is intact and accordingly if the power supply is OFF, the system assumes that the main connector is not connected with the MCU.

In an embodiment, if the main connector is not connected to the main control unit, at step 3028, the system verifies whether the micro-switch which, in an embodiment, is integrated within the electrical connector portion of the main connector, is depressed. If it can be verified that the micro-switch is depressed, in an embodiment, the system periodically restarts the detection process from the beginning of the verification cycle at step 3026 to ensure that it should not be in an alarm condition. In one embodiment, the duration between verification cycles is predetermined. In one embodiment, the duration between verification cycles can be set manually or programmed by the operator. If the micro-switch is not depressed, a signal indicative of the same is transmitted to the beeper/LED control unit as shown in step 3030. In an embodiment, if it is determined that the micro-switch is not depressed, the beeper/LED control unit activates an alarm system comprising either one or both of the visual LED or sound beeper as shown in step 3032 to notify the user that the connector cover cup is missing from the main connector of the endoscope. In an embodiment, once the alarm system is activated, the detection system stops the alarm after a pre-defined time period and restarts the detection process from step 3026 to verify whether the main connector is still not connected with the main control unit and the connector cover cup is still not positioned thereon.

Figure 3D:
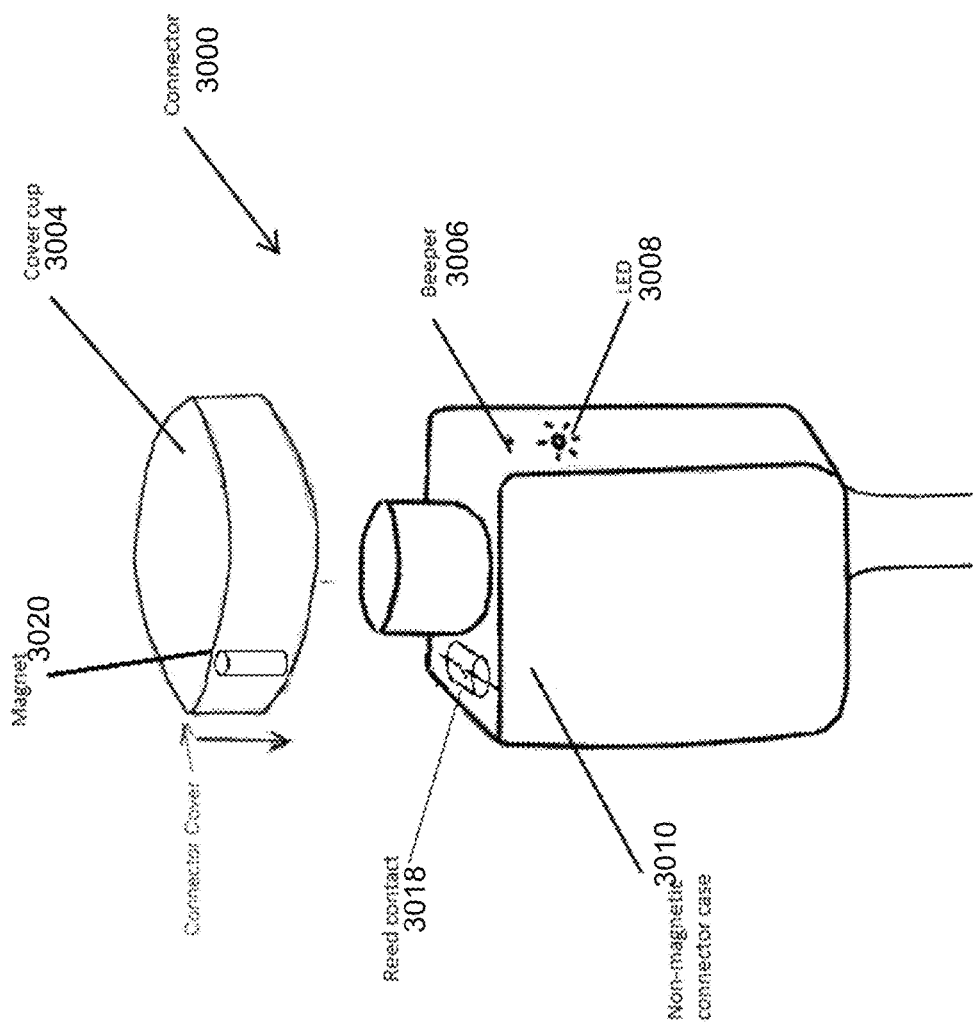
FIG. 3D illustrates an electrical connector comprising a reed contact with magnetic system for detecting the absence of a connector cover cup, in accordance with an embodiment of the present specification.

FIG. 3D illustrates an electrical connector comprising a reed contact with a magnetic system for detecting an absence of a connector cover cup, in accordance with an embodiment of the present specification. A reed switch is an electrical switch operated by an applied magnetic field. It consists of a pair of contacts formed on ferrous metal reeds contained within a hermetically sealed glass envelope. The contacts are originally in a first position and move to a second position when exposed to a magnetic field. Thus, the contacts may be originally in a first, open position and move to a second, closed position upon the presence of a magnetic field or originally in a first, closed position and move to a second, open position when a magnetic field is applied. Once the magnet is pulled away from the switch, the reed switch reverts to its first, original position.

As shown in FIG. 3D, a reed switch contact 3018 is provided on a top end of a main electrical connector 3000 of an endoscope. A connector cover cup 3004 comprises a corresponding magnet 3020. In an embodiment, when the connector cover cup 3004 is placed on the connector 3000, the magnet 3020 is brought in close proximity to the reed contact 3018, causing the reed contact 3018 to be in a first position, and transmits a signal indicative of an OFF condition to sound alarm/beeper 3006 and visual alarm/LED 3008 through a control logic/unit embedded in the non-magnetic connector case 3010. The control logic prevents occurrence of an alarm via the sound alarm/beeper 3006 and visual alarm/LED 3008 upon receiving a signal indicative of an OFF condition.

In an embodiment, when the connector cover cup 3004 is not placed on the connector 3000, as the magnet 3020 is away from the reed contact 3018, the reed contact 3018 moves from a first position to a second position and transmits a signal indicative of an ON condition to sound alarm/beeper 3006 and visual alarm/LED 3008 through the control logic thereby causing the sound alarm beeper 3006 to beep and the LED 3008 to emit light, for providing a warning alarm indicating the absence of the connector cover cup 3004.

In an embodiment, when the connector 3000 is inserted in the main control unit (MCU), the MCU regulates the functioning of control logic coupled to the warning system comprising the beeper 3006 and LED 3008. There are multiple methods through which the MCU can control the functioning of the warning system described above when the connector 3000 is inserted in and connected to the MCU. In an embodiment, when coupled with the connector 3000, the MCU enables a signal indicative of an OFF condition to be transmitted to the warning system through the control logic coupled to the warning system and switches off the beeper 3006 and LED 3008. In other embodiment, when the connector 3000 is inserted in the MCU, the MCU causes the power supply to the control unit to be disabled which causes the warning system to automatically turn off. In another embodiment, the MCU also comprises a magnet such as the magnet 3020 contained in the connector cover cup 3004 such that when the connector 3000 is inserted in the MCU, the magnet contained in MCU is brought in close proximity to the reed contact 3018, causing the reed contact 3018 to move back to a first position, and transmits a signal indicative of an OFF condition to sound alarm/beeper 3006 and visual alarm/LED 3008 through the control logic/unit embedded in the non-magnetic connector case 3010.

In the embodiment described above, the reed switch transmits a signal indicative of an "OFF" condition while it is in a first position and transmits a signal indicative of an "ON" condition when it goes from a first position to a second position. However, it should be appreciated by those skilled in the art that the nomenclature pertaining to "ON" or "OFF" conditions and relative positions are for purpose of illustration and that these indicators may be switched depending upon the programming of the control logic. A power supply module comprising a high capacitance capacitor or an accumulator is also installed within the connector 3000 for powering the sound alarm/beeper 3006 and LED 3008, the reed contact 3018 and the control logic.

In an embodiment, when the cover cup 3004 is positioned on the connector 3000, the signal indicative of an OFF condition transmitted from the reed contact 3018 to the control logic also causes the detection system to hibernate in order to minimize power consumption from the power supply. In an embodiment, the control logic comprises a timer that prevents an alarm occurrence during a predefined time interval when the connector 3000 is disconnected from the main control unit and the connector cover 3004 is put on. In another embodiment, the connector 3000 comprises a means to manually switch off the warning alarm to accommodate for the situations in which the connector cover cap is misplaced by the user or an alarm is otherwise not needed.

Figure 3E:
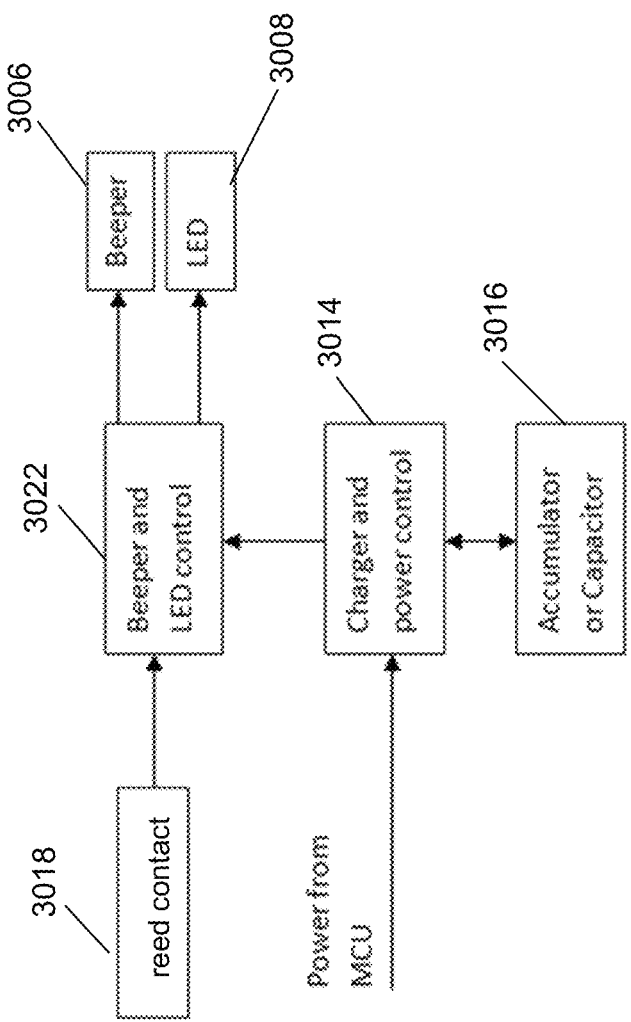
FIG. 3E is a block diagram illustrating the connectivity of components for detecting the absence of a connector cover cup by using a reed contact with magnetic system, in accordance with an embodiment of the present specification.

FIG. 3E is a block diagram illustrating the connectivity of components for detecting the absence of a connector cover cup by employing a reed contact with magnetic system, in accordance with an embodiment of the present specification. The reed contact 3018 is connected to a beeper and LED control unit 3022 which in turn is connected to the sound alarm/beeper 3006 and visual alarm/LED 3008. In an embodiment, when the reed contact 3018 is in proximity of a corresponding magnet it is in a first position and transmits a signal indicative of an OFF condition to the control unit 3022 which in turns keeps the warning system comprising the beeper 3006 and LED 3008 switched off. In an embodiment, when the main connector is not connected with the MCU, and the connector cover cup 3004 is not secured over the connector 3000, the reed contact 3018 moves to a second position and transmits a signal indicative of an ON condition to the control unit 3022 which activates the warning system comprising the sound alarm 3006 and LED 3008. However, in an embodiment, when the connector cover cup is secured over the main connector, the magnet contained in the connector cover cup causes the reed contact to move from a second position to a first position and transmit a signal indicative of an OFF condition to the control unit 3022 which accordingly switches off the beeper 3006 and LED 3008.

In an embodiment, the endoscope system comprises a charger and power control unit 3014 which is connected to a power supply module 3016 and regulates the power to the control unit 3022. In an embodiment, when the main connector is connected with the main control unit (MCU), the power from the MCU charges the power supply module 3016 comprising an accumulator or a capacitor via the charger and power control unit 3014. In an embodiment, the charger and power control unit 3014 regulates the current supply to the power supply module 3016 and once the system is fully charged, it disconnects the current supply to power supply module 3016 to prevent overcharging.

In an embodiment, when the connector 3000 is connected with the MCU, the MCU controls the functioning of control unit 3022 and therefore, controls the warning system comprising the beeper 3006 and LED 3008. In an embodiment, when the main connector is connected with the MCU, the MCU transmits a signal indicative of an OFF condition to the control unit 3022 through the charger and power control unit 3014. The control unit 3022 receives the signal indicative of an OFF condition and accordingly switches off the warning system comprising alarm 3006 and LED 3008. In other embodiment, the MCU instructs the charger and power control unit 3014 to simply disable the power supply to the control unit 3022 causing the warning system to automatically switch off. In another embodiment, the MCU also comprises a magnet such as the magnet 3020 contained in the connector cover cup 3004 illustrated in FIG. 3D such that when the connector 3000 is inserted in the MCU, the magnet contained in MCU is brought in close proximity to the reed contact 3018, causing the reed contact 3018 to move back to a first position, and transmits a signal indicative of an OFF condition to sound alarm/beeper 3006 and visual alarm/LED 3008 through the control logic/unit embedded in the non-magnetic connector case.

Figure 3F:
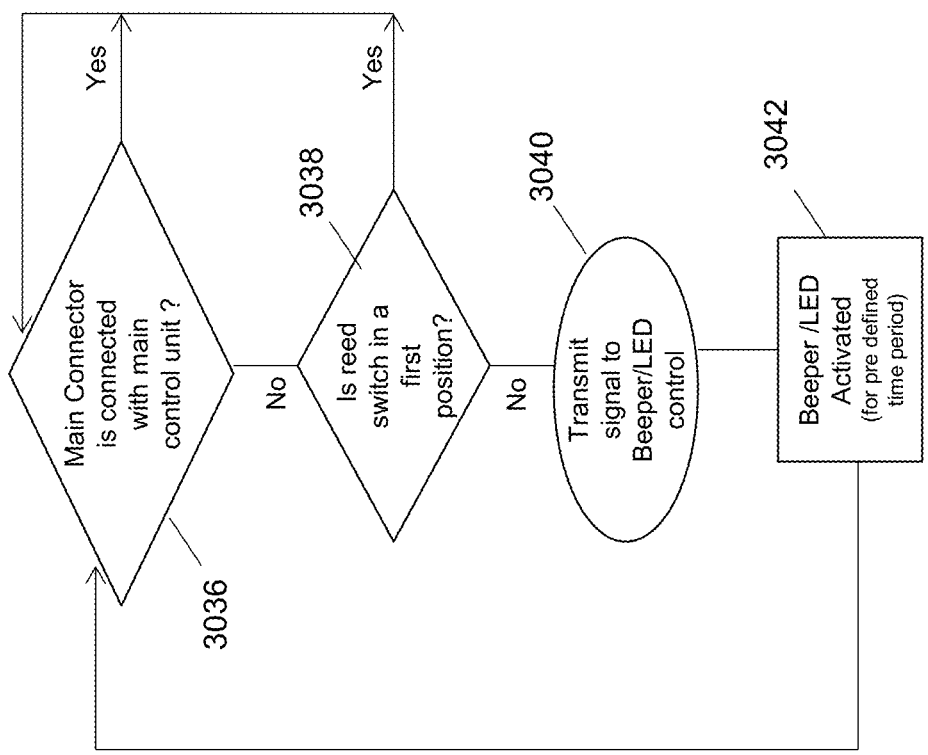
FIG. 3F illustrates a flow chart of the steps implemented by the detection and notification system using a reed contact with magnetic system, in accordance with an embodiment of the present specification.

FIG. 3F illustrates a flow chart of the steps implemented by the detection and notification system employing a reed contact with a magnetic switch in accordance with an embodiment of the present specification. As shown in FIG. 3F, at step 3036, the detection system checks if the main connector of the endoscope assembly is connected with the main control unit. If the main connector is connected with the main control unit, in an embodiment, the system iteratively checks that this connection is intact. In another embodiment, once it is confirmed that the connection between the main connector and the main control unit is intact, the system iteratively rechecks the connection after a pre-defined time interval. Thus, in an embodiment, the process is cyclical and this check is performed periodically. In an embodiment, the above check is performed by detecting the status of power supply coming from MCU. In an embodiment, the MCU provides the power supply to the endoscope assembly through the charger and power control module 3014 present in the connector 3000 as illustrated in FIG. 3E. In an embodiment, the connector 3000 comprises a means to detect whether the power supply from MCU is ON or OFF. In case the power supply is ON, the system assumes that the connection between connector and MCU is intact and accordingly if the power supply is OFF, the system assumes that the main connector is not connected with the MCU.

In an embodiment, if the main connector is not connected with the main control unit, at the next step 3038, the system determines whether the reed switch, which, in an embodiment, is integrated with the electrical connector portion of the main connector, is in a first position. In the above embodiment, when the reed switch is in a first position, it signifies that either the main connector is connected with the main control unit or the connector cover cup is attached to the main connector. If it is determined that the reed switch is in a first position, in an embodiment, the system restarts the detection process from the beginning of the verification cycle, meaning at step 3036 to ensure that it should not be in an alarm condition.

If the reed switch is not in a first position and has moved to a second position, a signal indicative of the same is transmitted to the beeper/LED control unit as shown in step 3040. In an embodiment, once it is determined that the reed switch is not in an original position, the beeper/LED control unit activates an alarm system comprising either one or both of the visual alarm/LED or audible alarm/beeper as shown in step 3042 to notify the user that the connector cover cup is missing from the main connector of endoscope. In an embodiment, once the alarm system is activated, the detection system stops the alarm after a pre-defined time period and again starts the detection process from step 3036 to ensure that the main connector is still not connected with the main control unit and that the connector cover cup is still missing.

Figure 4A:
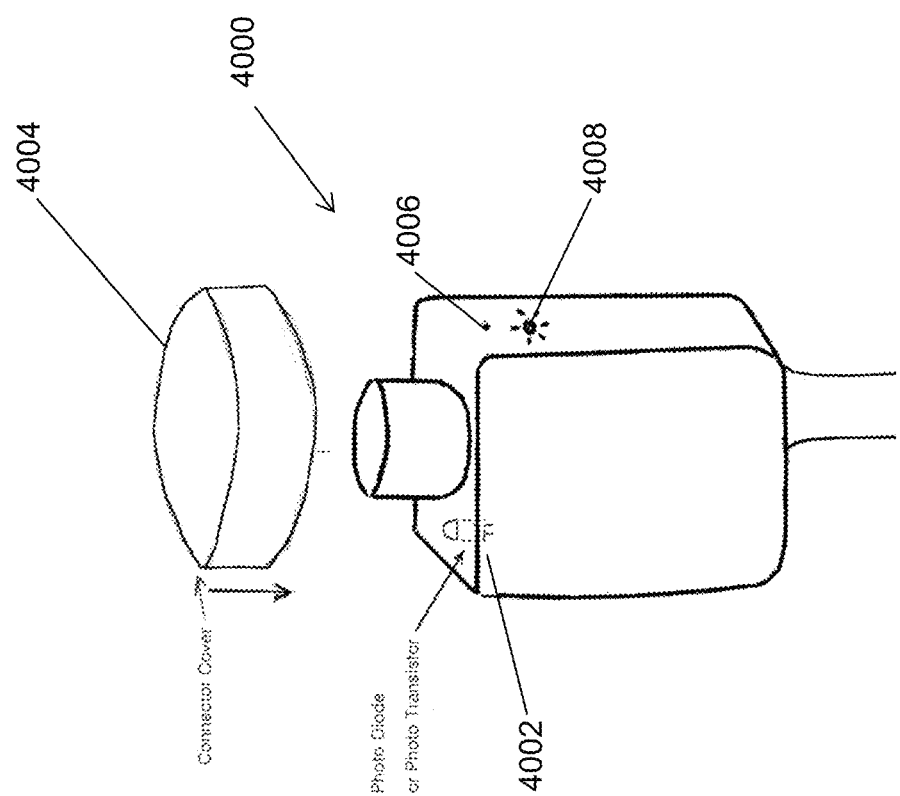
FIG. 4A illustrates an electrical connector comprising a photodiode/phototransistor for detecting an absence of a connector cover cup, in accordance with an embodiment of the present specification.

FIG. 4A illustrates an electrical connector comprising a photodiode/phototransistor for detecting an absence of a connector cover cup, in accordance with an embodiment of the present specification. As illustrated in FIG. 4A, a photodiode/phototransistor 4002 is provided on a top end of a main electrical connector 4000 of an endoscope. When a connector cover cup 4004 is positioned over the connector 4000 and any external light (from room lighting for example) does not fall on photodiode/phototransistor 4002, the photodiode/phototransistor 4002 is deactivated, breaking a connection that activates audible alarm/beeper 4006 and visual alarm/LED 4008. In an embodiment, the connection is also breached when the electrical connector 4000 is plugged into a main control unit of the endoscope.

In other embodiment, when the electrical connector 4000 is plugged in a MCU, the MCU regulates the warning system comprising beeper 4006 and LED 4008 through a control logic coupled with the warning system. In an embodiment, the MCU causes the power supply to the control logic to be disabled which automatically switches off the warning system. In other embodiment, the MCU transmits a signal indicative of an OFF condition to the control logic which on receiving such signal disables the warning system.

When the connector cover cup 4004 is not attached with the connector 4000 and when the connector 4000 is not plugged into the main control unit, the photodiode/phototransistor 4002 is coupled with the audible alarm/beeper 4006 and LED 4008, thus causing the audible alarm 4006 to produce a sound and/or the LED 4008 to emit light triggering a warning alarm indicating the absence of the connector cover cup 4004.

Figure 4B:
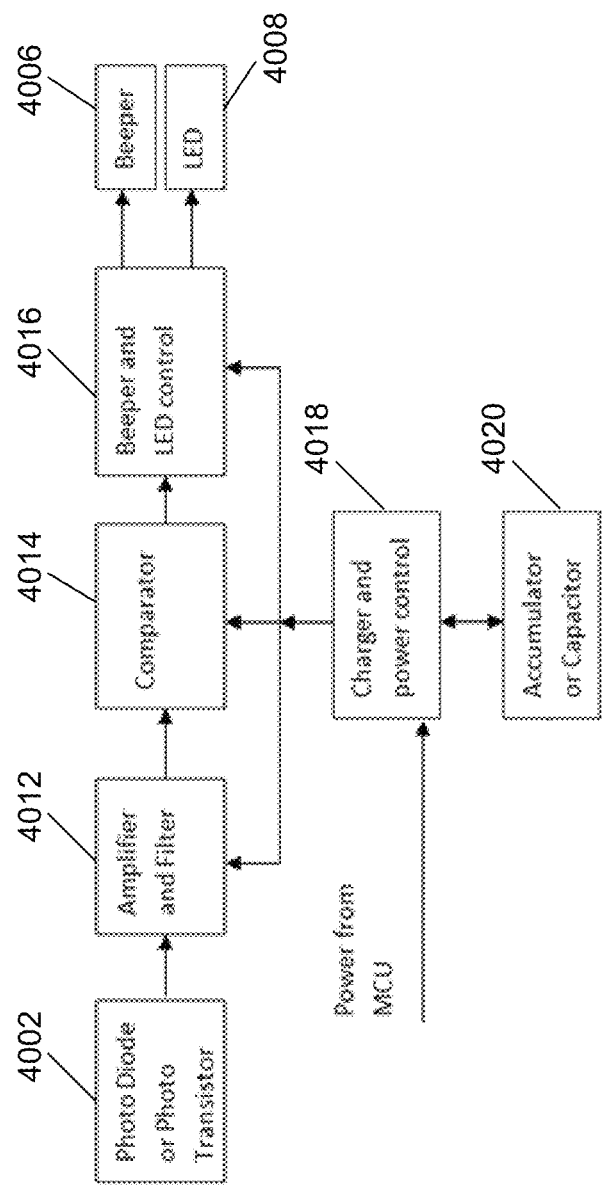
FIG. 4B is a block diagram illustrating the connectivity of components for detecting the absence of a connector cover cup by using a photodiode/phototransistor, in accordance with an embodiment of the present specification.

FIG. 4B is a block diagram illustrating the connectivity of components for detecting the absence of a connector cover cup by employing a photodiode/phototransistor, in accordance with an embodiment of the present specification. A photosensitive device such as a photodiode/phototransistor 4002 is connected to an amplifier and filter unit 4012 which is connected to an audible alarm/beeper and LED control unit 4016 via a comparator 4014. The control unit 4016 is further connected to the audible alarm/beeper 4006 and LED 4008. In an embodiment, when photodiode/phototransistor 4002 is exposed to light from an external light source (e.g. ambient light), the photodiode/phototransistor 4002 emits a signal that is amplified and filtered by the amplifier and filter 4012. This occurs when both the connector cover cup 4004 is not positioned over the main connector 4000 and the main connector 4000 is not connected to the main control unit of the endoscope. The comparator 4014 compares the amplified and filtered signal with a benchmark signal having a pre-defined level. In an embodiment, when the signal level output by the amplifier and filter 4012 is higher than that that of the benchmark signal, the audible alarm/beeper and LED control unit 4016 activates the audible alarm 4006 to produce a sound and the visual alarm/LED 4008 to emit light, thereby providing a warning alarm indicating the absence of the connector cover cup 4004.

When photodiode/phototransistor 4002 is not exposed to light from an external or ambient light source, which happens when the connector cover cup 4004 is positioned over the connector 4000 or the connector 4000 is plugged into a main control unit of an endoscope, the signal level output by the photodiode/phototransistor 4002 is subsequently amplified and filtered by the amplifier and filter 4012 and is lower than the level of predefined benchmark signal. The comparator 014 compares the two signals and as the signal level output by the amplifier and filter 4012 is lower than the level of predefined benchmark signal, the alarm control unit 4016 does not activate the audible alarm 4006 to produce a sound and the visual alarm/LED 4008 to emit light, thereby preventing occurrence of an alarm.

In another embodiment, when the main connector 4000 is connected to a MCU, the MCU regulates the control unit 4016. In an embodiment, the MCU transmits a signal indicative of an OFF condition to the control unit 4016 which on receiving such signal switches off the warning system comprising the beeper 4006 and LED 4008. In other embodiment, the MCU causes the power supply to the control unit 4016 to be disabled which automatically switches off the warning system.

In an embodiment, a charger and power control unit 4018 connected to a power supply module, such as an accumulator or capacitor 4020, powers the audible alarm/beeper and visual alarm/LED control unit 4016. When the main connector 4000 is connected to a main control unit (MCU) of the endoscope, power from the MCU charges the accumulator or capacitor 4020. When the connector 4000 is connected with the main control unit, the changer and power control unit 4018 limits the accumulator/capacitor 4020 charging current, and once the system is fully charged, it also disconnects the accumulator or capacitor 4020 in order to prevent overcharging.

In an embodiment, when the main connector 4000 is connected to a MCU, the MCU regulates various components such as photodiode or transistor 4002, amplifier 4012 and comparator 4014 such that these components are shutdown/switched off to reduce the power consumption by the system.

Figure 4C:
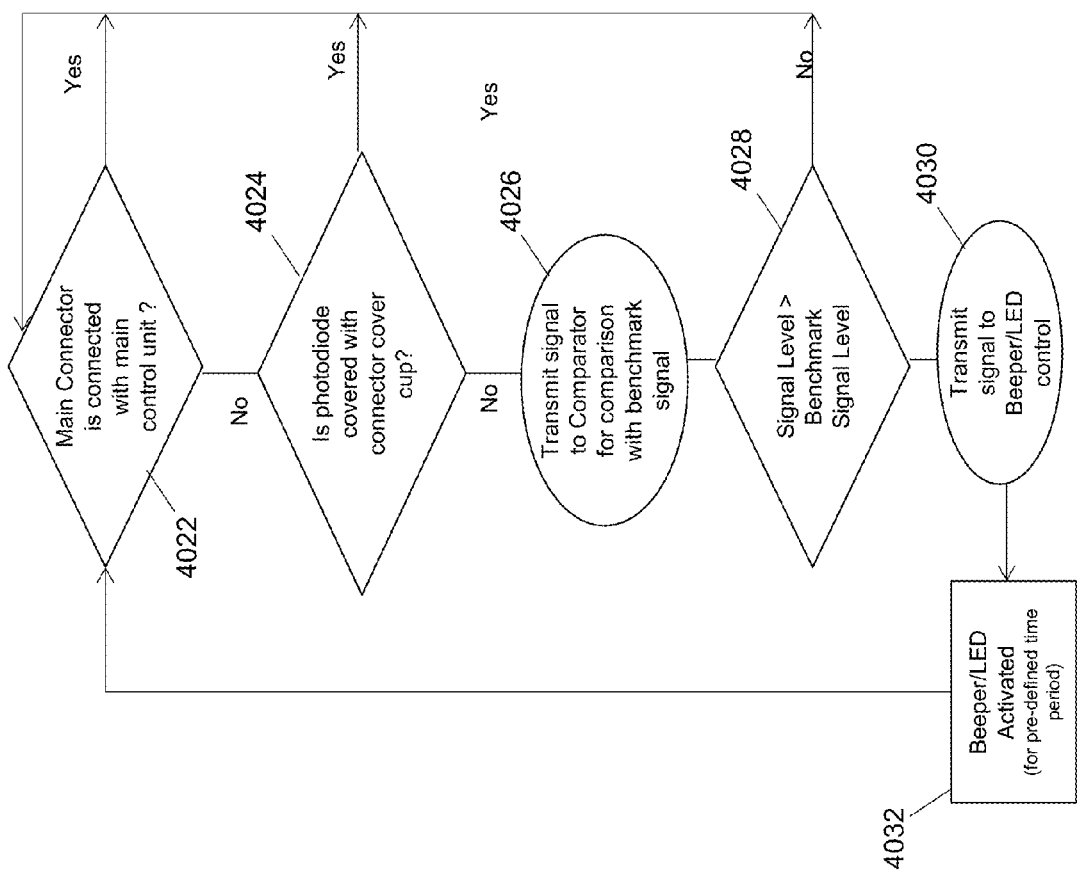
FIG. 4C illustrates a flow chart of the steps implemented by the detection and notification system when employing a photodiode in accordance with an embodiment of the present specification.

FIG. 4C illustrates a flow chart of the steps implemented by the detection and notification system employing a photodiode/phototransistor in accordance with an embodiment of the present specification. As shown in FIG. 4C, at step 4022, the detection system checks if the main connector of the endoscope assembly is connected to the main control unit. If the main connector is connected to the main control unit, in an embodiment, the system iteratively checks that this connection is intact. In another embodiment, once it is confirmed that the connection between the main connector and the main control unit is intact, the system iteratively rechecks the connection, beginning at step 4022 after a pre-defined time interval. Thus, in an embodiment, the process is cyclical and this check is performed periodically. In an embodiment, the above check is performed by detecting the status of power supply coming from MCU. In an embodiment, the MCU provides the power supply to the endoscope assembly through the charger and power control module 4018 contained in the connector 3000 as illustrated in FIG. 4C. In an embodiment, the connector 4000 comprises a means to detect whether the power supply from MCU is ON or OFF. In case the power supply is ON, the system assumes that the connection between connector and MCU is intact and accordingly if the power supply is OFF, the system assumes that the main connector is not connected with the MCU.

In an embodiment, if the main connector is not connected to the main control unit, at step 4024, the system verifies whether the photodiode which, in an embodiment, is integrated within the electrical connector portion of the main connector, is covered with the connector cover cup. In case the photodiode is covered with the connector cover cup, in an embodiment, the system periodically restarts the detection process from the beginning of the verification cycle at step 4022 to ensure that it should not be in an alarm condition. In one embodiment, the duration between verification cycles is predetermined. In one embodiment, the duration between verification cycles can be set manually or programmed by the operator.

If the photodiode is not covered with the connector cover cup, a signal indicative of the same is transmitted to a comparator to find whether the strength of signal transmitted by the photodiode is higher than that of the benchmark signal as shown in step 4026. At step 4028, the system compares the two signal levels. In case the strength of signal transmitted by photodiode is lower than the strength of benchmark signal, in an embodiment, it is interpreted as noise and the system periodically restarts the detection process from the beginning of the verification cycle at step 4022 to ensure that it should not be in an alarm condition. In case the strength of signal transmitted by the photodiode is higher than the strength of the benchmark signal, a signal indicative of the same is transmitted to the alarm control unit as shown in step 4030.

In an embodiment, if it is determined that the photodiode is active, the alarm control unit activates an alarm system comprising either one or both of the visual LED or sound beeper as shown in step 4032 to notify the user that the connector cover cup is missing from the main connector of the endoscope. In an embodiment, once the alarm system is activated, the detection system stops the alarm after a pre-defined time period and restarts the detection process from step 4022 to verify whether the main connector is still not connected with the main control unit and the connector cover cup is still not positioned thereon.

Figure 5A:
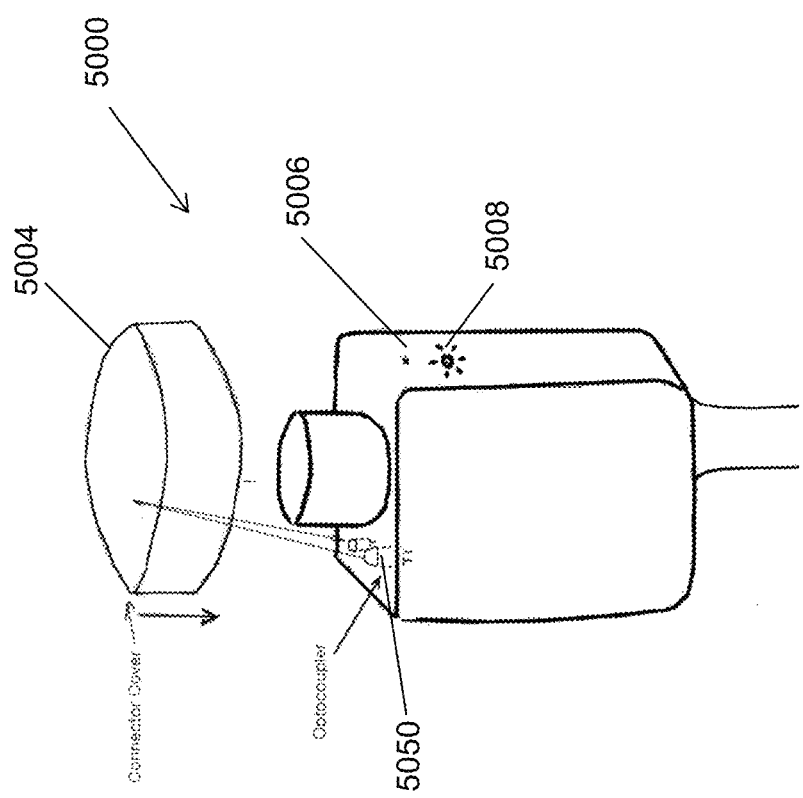
FIG. 5A illustrates an electrical connector comprising an optocoupler for detecting an absence of a connector cover cup, in accordance with an embodiment of the present specification.

FIG. 5A illustrates an electrical connector comprising an optocoupler for detecting an absence of a connector cover cup, in accordance with an embodiment of the present specification. As illustrated in FIG. 5A, an optocoupler 5050 is provided on a top end of a main electrical connector 5000 of an endoscope. When a connector cover cup 5004 is positioned over the connector 5000, a light beam emitted by an LED section of the optocoupler 5050 is reflected by the connector cover 5004 causing the light beam to return to a photosensitive section of the optocoupler 5050, which deactivates/breaks a connection that activates the audible alarm/beeper 5006 and LED 5008. The connection is also broken when the electrical connector 5000 is plugged into a main control unit of the endoscope.

In other embodiment, when the electrical connector 5000 is plugged in a MCU, the MCU regulates the warning system comprising beeper 5006 and LED 5008 through a control logic coupled with the warning system. In an embodiment, the MCU causes the power supply to the control logic to be disabled which automatically switches off the warning system. In other embodiment, the MCU transmits a signal indicative of an OFF condition to the control logic which on receiving such signal disables the warning system.

When the connector cover cup 5004 is not positioned over the connector 5000 and the connector 5000 is also not plugged into the main control unit, a light beam emitted by an LED section of the optocoupler 5050 is not returned to a photosensitive section of the optocoupler 5050 and the connection that activates the alarm unit remains intact causing the audible alarm beeper 5006 to beep and the LED 5008 to emit light, thereby providing a warning alarm indicating the absence of the connector cover cup 5004. In an embodiment, the optocoupler 5050 is an infrared optocoupler with optic lenses.

Figure 5B:
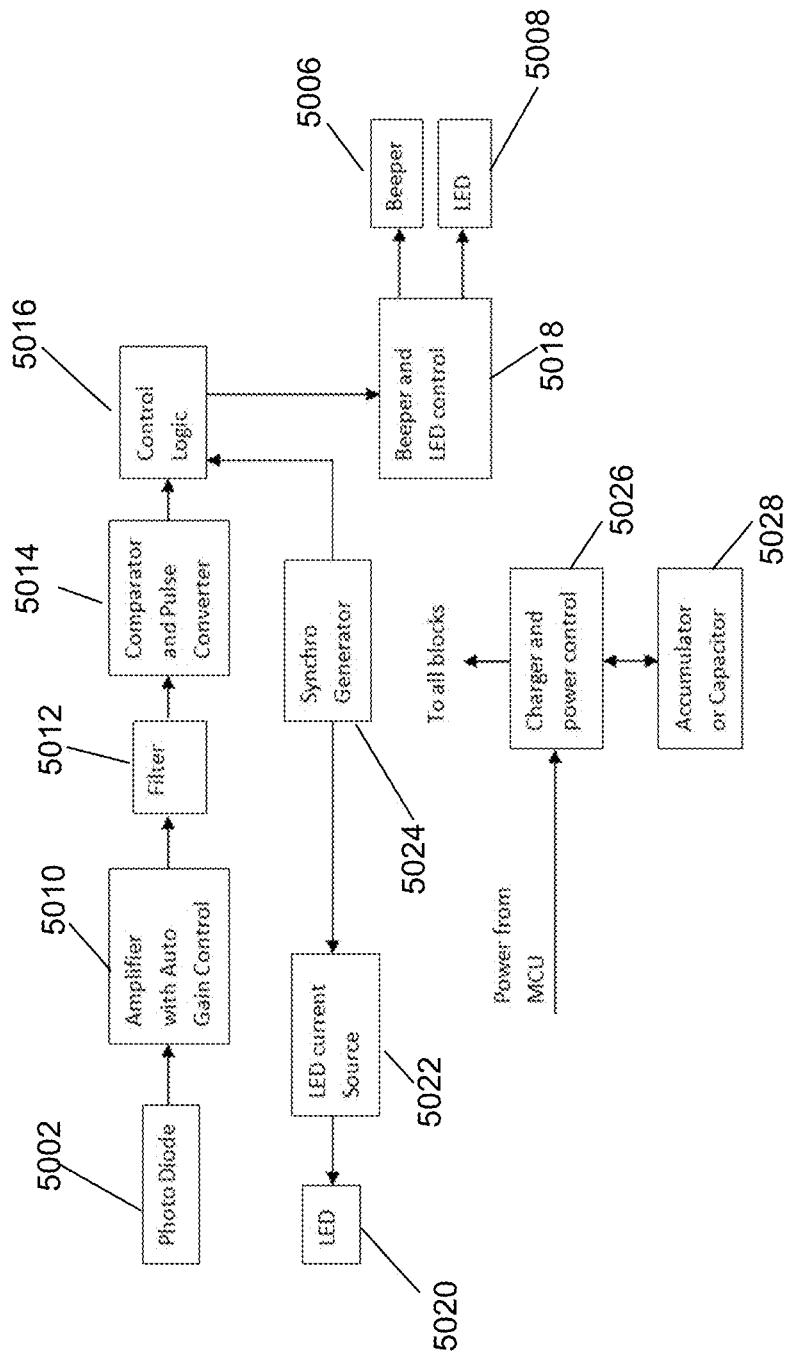
FIG. 5B is a block diagram illustrating the connectivity of components for detecting an absence of a connector cover cup by using an optocoupler, in accordance with an embodiment of the present specification.

FIG. 5B is a block diagram illustrating the connectivity of components for detecting the absence of a connector cover cup by employing a optocoupler in accordance with an embodiment of the present specification. As illustrated in FIG. 5B, an optocoupler is shown which comprises a photosensitive section such as a photodiode 5002 connected to an amplifier with auto gain control unit 5010 which is connected to a audible alarm/beeper and LED control unit 5018 via a filter 5012, a comparator and pulse converter 5014 and a control logic 5016. The control logic 5016 is coupled with a synchro-generator 5024 which is in turn coupled with an LED section 5020 of the optocoupler via an LED current source 5022.

The LED 5020 of optocoupler is an infra-red light source powered through the LED current source 5022 which supplies a constant current to the LED 5020. The synchro-generator 5024 generates a signal which is created by performing high frequency modulation of current signal being supplied to the LED 5020. The modulation enables separation between signals of the photosensitive section 5002 of the optocoupler produced due to light beam emitted by the LED section 5020 of optocoupler and signals produced by photosensitive section 5002 on receiving the noise signals.

The amplifier with auto gain control 5010 amplifies signals produced by the photo sensitive section 5002 of the optocoupler with gain optimal for specific environment, that further helps in distinguishing between signals of the photosensitive section 5002 produced due to light beam emitted by the LED section 5020 and those produced due to noise signals. The amplifier with auto gain control 5010 also performs the function of impedance matching between the very high impedance of optocoupler's photosensitive section 5002 and a lower impedance of filter 5012. In an embodiment, the filter 5012 is adjusted to the frequency of synchro generator 5024. The comparator and pulse converter 5014 compares the output signal level of the filter 5012 with a predefined threshold signal and produces a high level signal, when the output filter signal is higher than the predefined threshold signal, and a low level signal, when the output filter signal is lower than the predefined threshold signal.

The control logic 5016 verifies that the signal output by the comparator and pulse converter 5014 and the signal output by the synchro generator 5024 rise and fall in same time to confirm that the optocoupler's photosensitive section 5002 reacts in response to the light beam that is produced by the LED section 5020 and is returned after reflection from the connector cover cup 5004 positioned over the connector 5000, and not in response to any signal received from an external noise source (for example an ambient light source). When the cover cup 5004 is put on the connector 5000 or when the connector 5000 is connected to the main connector of an endoscope, the control logic 5016 produces a signal which is input to the beeper and LED control 5018, to prevent an acoustic and visible alarm produced by the beeper 5006 and LED 5008 respectively. In an embodiment, the control logic 5016 comprises a timer that prevents an alarm occurrence during the short time interval when the connector 5000 is disconnected from the main control unit and the connector cover 5004 is put on.

In another embodiment, when the main connector 5000 is connected to a MCU, the MCU regulates the control unit 5016. In an embodiment, the MCU transmits a signal indicative of an OFF condition to the control unit 5016 which on receiving such signal switches off the warning system comprising the beeper 5006 and LED 5008. In other embodiment, the MCU causes the power supply to the control unit 5016 to be disabled which automatically switches off the warning system.

When the optocoupler's photosensitive section 5002 does not receive any signal from the LED section 5020, the connection that activates the audible alarm/beeper and LED control unit 5018 remains intact and, the beeper 5006 and the LED 5008 are activated to produce sound and emit light respectively. This happens when the connector cover cup 5004 is not put on the main connector 5000 and the connector 5000 is also not connected to a main control unit of the endoscope. A charger and power control unit 5026 connected to a power supply such as an accumulator or capacitor 5028 powers all the remaining components of the system as illustrated in FIG. 5B. When the main connector 5000 is connected to a main control unit (MCU) of the endoscope, power from the MCU charges the accumulator or capacitor 5028 via the power control unit 5026. When the connector 5000 is connected to the main control unit, the changer and power control unit 5026 limits the accumulator/capacitor 5028 charging current, once the system is fully charged, it also disconnects the accumulator or capacitor 5028 in order to prevent overcharging.

In an embodiment, when the main connector 5000 is connected to a MCU, the MCU regulates various components like photodiode 5002, amplifier 5010, filter 5012, comparator and pulse converter 5014, LED 5020, LED current source 5022, synchro generator 5024 and control unit 5016 such that these components are shutdown/switched off to reduce the power consumption by the system.

Figure 5C:
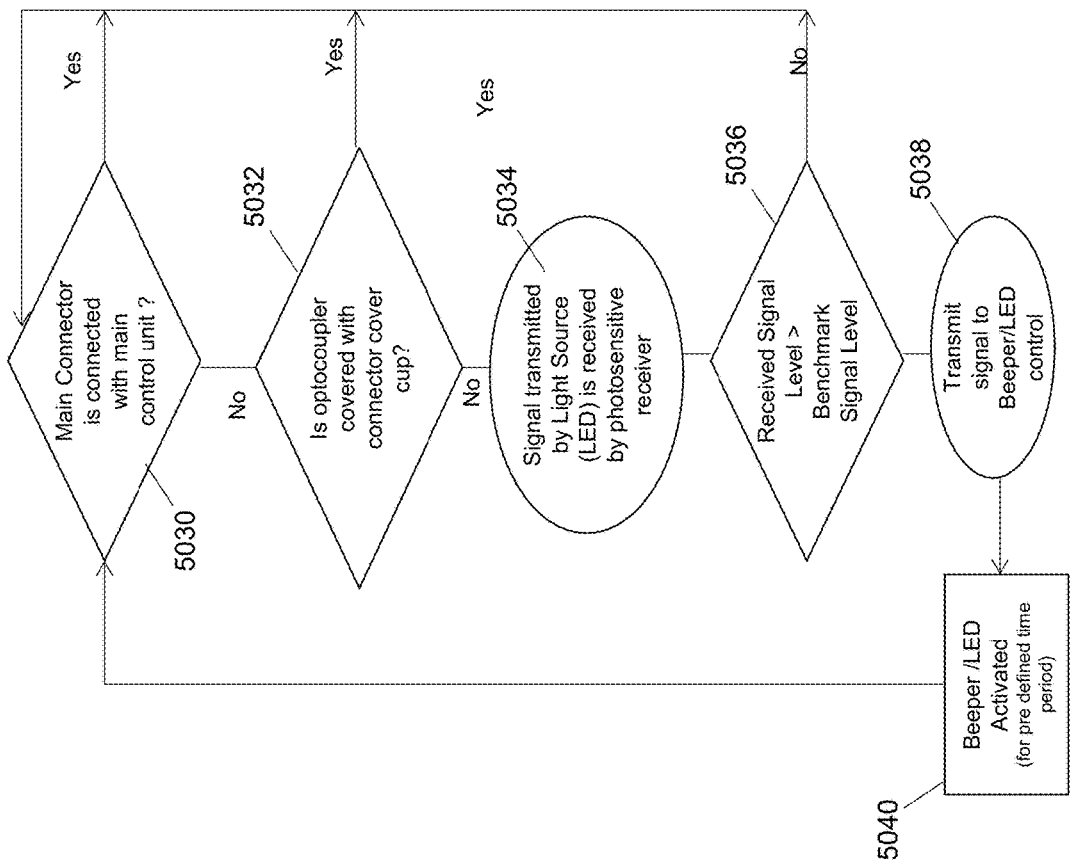
FIG. 5C illustrates a flow chart of the steps implemented by the detection and notification system when employing an optocoupler in accordance with an embodiment of the present specification.

FIG. 5C illustrates a flow chart of the steps implemented by the detection and notification system employing an optocoupler in accordance with an embodiment of the present specification. As shown in FIG. 5C, at step 5030, the detection system checks if the main connector of the endoscope assembly is connected to the main control unit. If the main connector is connected to the main control unit, in an embodiment, the system iteratively checks that this connection is intact. In another embodiment, once it is confirmed that the connection between the main connector and the main control unit is intact, the system iteratively rechecks the connection, beginning at step 5030 after a pre-defined time interval. Thus, in an embodiment, the process is cyclical and this check is performed periodically. In an embodiment, the above check is performed by detecting the status of power supply coming from MCU. In an embodiment, the MCU provides the power supply to the endoscope assembly through the charger and power control module 5026 as illustrated in FIG. 5B. In an embodiment, the connector 5000 comprises a means to detect whether the power supply from MCU is ON or OFF. In case the power supply is ON, the system assumes that the connection between connector and MCU is intact and accordingly if the power supply is OFF, the system assumes that the main connector is not connected with the MCU.

In an embodiment, if the main connector is not connected to the main control unit, at step 5032, the system verifies whether the optocoupler which, in an embodiment, is integrated within the electrical connector portion of the main connector, is covered with the connector cover cup. In case the optocoupler is covered with the connector cover cup, in an embodiment, the system periodically restarts the detection process from the beginning of the verification cycle at step 5030 to ensure that it should not be in an alarm condition. In one embodiment, the duration between verification cycles is predetermined. In one embodiment, the duration between verification cycles can be set manually or programmed by the operator.

If the optocoupler is not covered with the connector cover cup, at step 5034, a signal transmitted by the LED section of the optocoupler is received by the photosensitive section of the optocoupler. At step 5036, the system compares the received signal with a benchmark signal. In case the strength of signal received by photosensitive section of the optocoupler is lower than the strength of benchmark signal, in an embodiment, it is interpreted as noise and the system periodically restarts the detection process from the beginning of the verification cycle at step 5030 to ensure that it should not be in an alarm condition. In case the strength of signal received by the photosensitive section of the optocoupler is higher than the strength of the benchmark signal, a signal indicative of the same is transmitted to the beeper/LED control unit as shown in step 5038.

In an embodiment, if it is determined that the optocoupler is active, as measured from the strength of the signal received by the photosensitive section of optocoupler, the beeper/LED control unit activates an alarm system comprising either one or both of the visual LED or sound beeper as shown in step 5040 to notify the user that the connector cover cup is missing from the main connector of the endoscope. In an embodiment, once the alarm system is activated, the detection system stops the alarm after a pre-defined time period and restarts the detection process from step 5030 to verify whether the main connector is still not connected with the main control unit and the connector cover cup is still not positioned thereon.

Figure 6A:
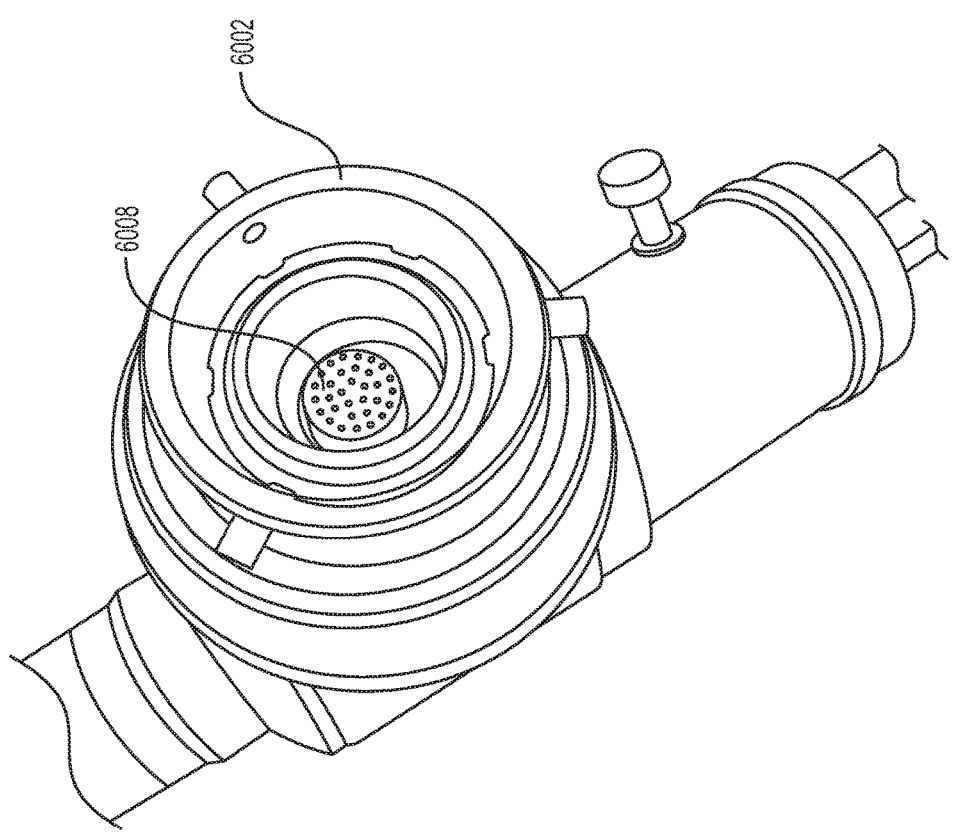
FIG. 6A illustrates a main connector of an endoscope, in accordance with an embodiment of the present specification.

FIG. 6A illustrates a main connector of an endoscope, in accordance with an embodiment of the present specification. Main connector 6002 connects the endoscope to a main control unit. The main connector 6002 comprises an electrical connector 6008 which provides the electrical and data communication link between the endoscope assembly and a main control unit of an endoscope.

FIG. 6B illustrates a connector cover cup, in accordance with an embodiment of the present specification. Connector cover cup 6004 comprises a bayonet lock and two o-rings 6010 and 6012 that provide a hermetic sealing.

Figure 6C:
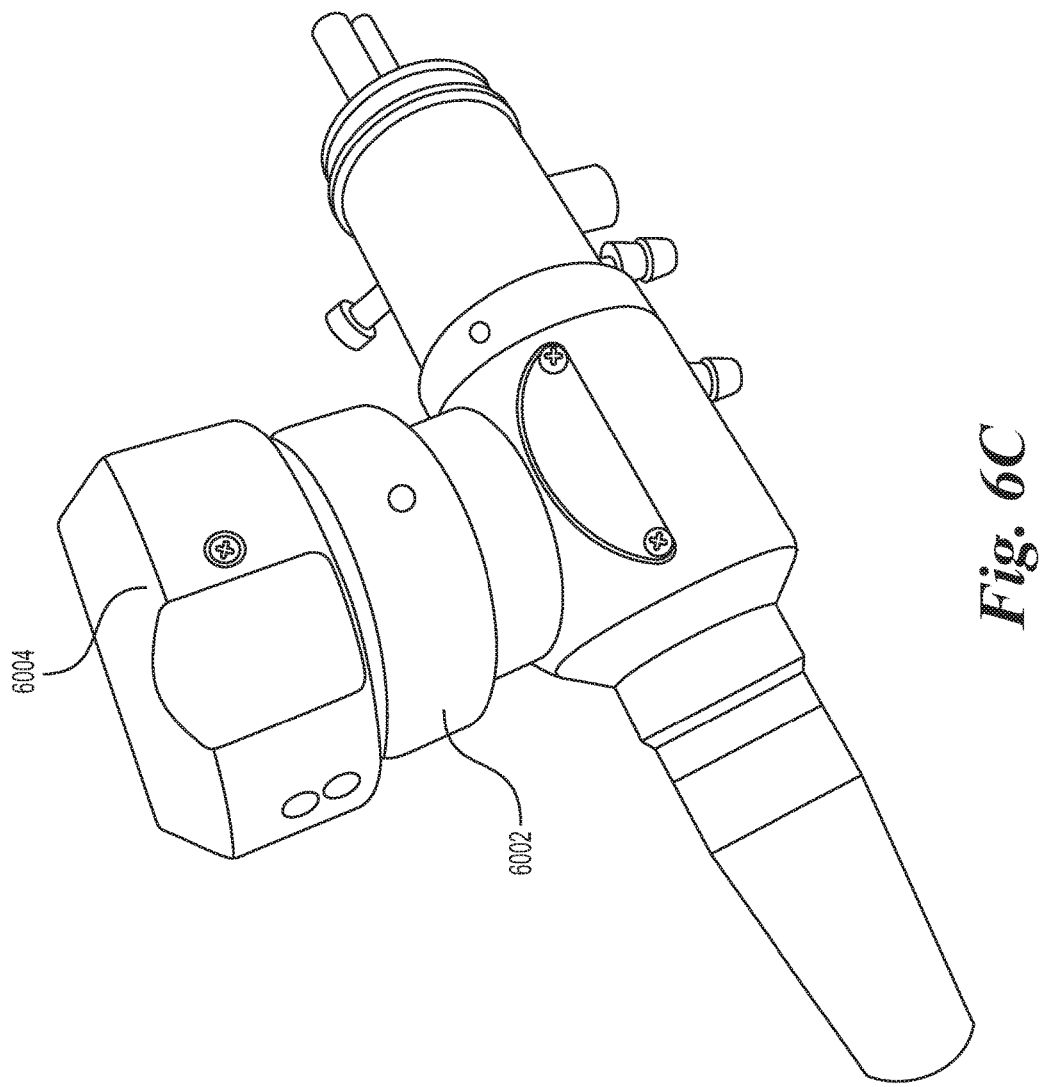
FIG. 6C illustrates a main connector of an endoscope covered with a connector cover cup, in accordance with an embodiment of the present specification.

FIG. 6C illustrates a main connector of an endoscope covered with a connector cover cup, in accordance with an embodiment of the present specification. The cover cup 6004 when put on the main connector 6002 prevents any water or other fluids from entering the main connector 6002 and causing damage, when the endoscope is being washed/cleaned.

Figure 6D:
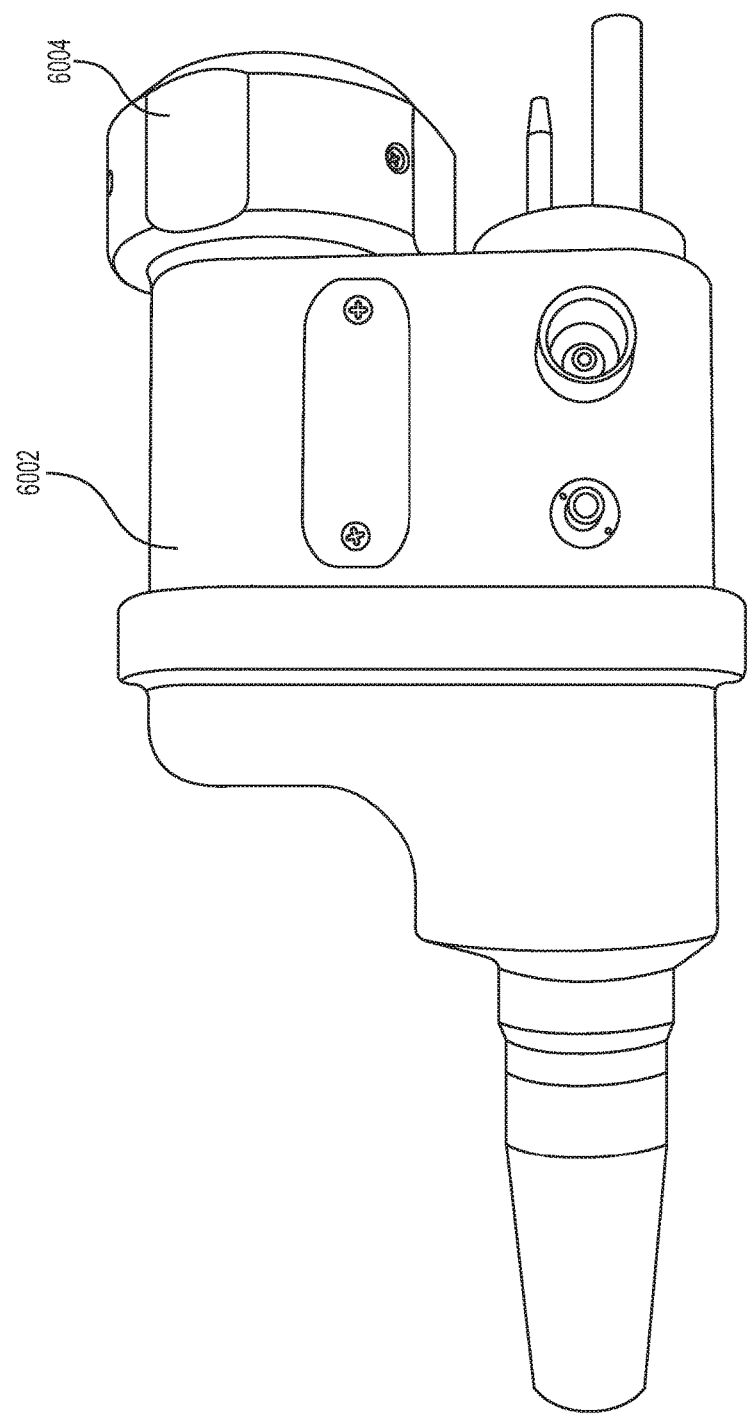
FIG. 6D illustrates a main connector of an endoscope, in accordance with another embodiment of the present specification; and, FIG. 6E illustrates an electrical connector of a main connector of an endoscope, in accordance with another embodiment of the present specification.
Figure 6E:
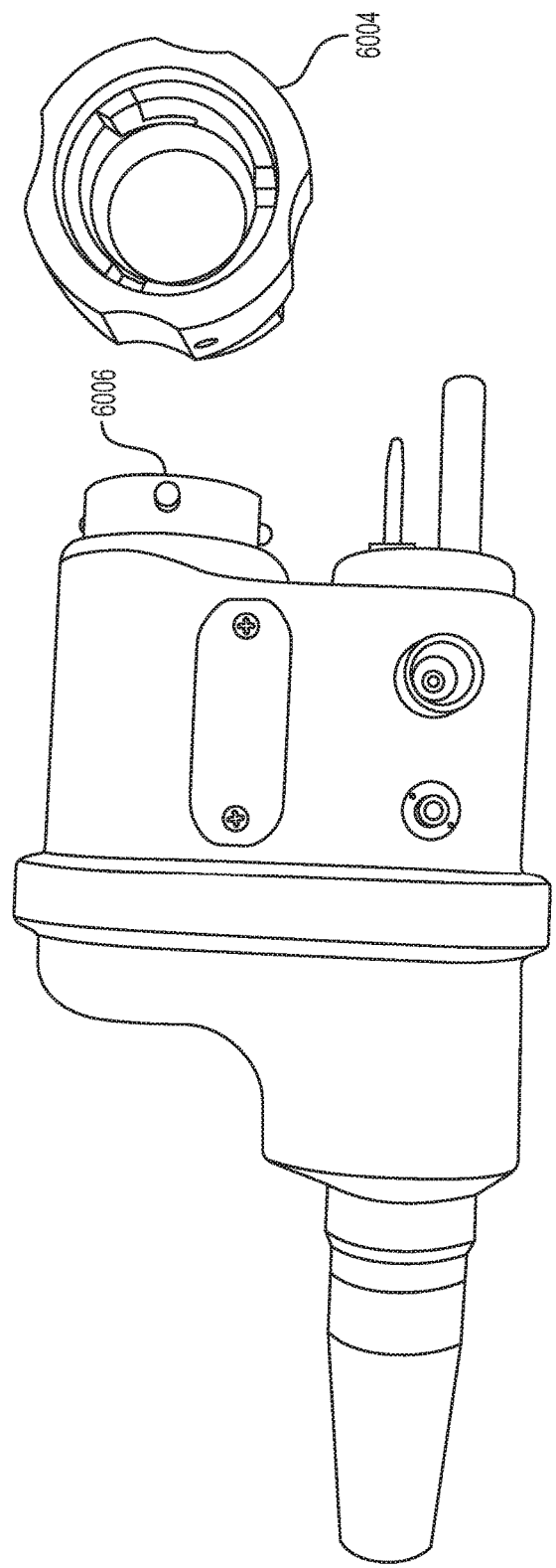
FIG. 6B illustrates a connector cover cup, in accordance with an embodiment of the present specification.

FIG. 6D illustrates a main connector of an endoscope, in accordance with another embodiment of the present specification. The main connector 6002 comprises an electrical connector 6006 (illustrated in FIG. 6E) that is used to electrically connect the endoscope to a main control unit. As shown in FIG. 6D, the electrical connector of the main connector 6002 is covered with a connector cover cup 6004, in accordance with an embodiment of the present specification. FIG. 6E illustrates an electrical connector of a main connector of an endoscope, in accordance with another embodiment of the present specification. The figure shows the connector cover cup 6004 removed from the electrical connector 6006 and thereby exposing the electrical connector 6006 of the main connector 6002.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

In the description and claims of the application, each of the words "comprise" "include" and "have", and forms thereof, are not necessarily limited to members in a list with which the words may be associated.

I claim:

1. An endoscope assembly, comprising:
   a handle;
   a connector for connecting the endoscope assembly to an endoscope control unit, the connector including a fixed end fixed to the handle, and a free end opposite the fixed end, the free end being configured to be received in and entirely withdrawn from the endoscope control unit; and
   a warning system for indicating an absence of a connector cover, the connector cover being adapted to cover said free end of the connector, when said connector is not connected to the endoscope control unit, the warning system comprising:
      an alarm unit configured to emit at least one of light and sound from the free end of the connector,
      a power source in the free end of the connector for powering the alarm unit, and
      a detection system in the free end of the connector for detecting said absence of the connector cover on top of said free end of the connector, and activating the alarm unit if the connector cover is absent from said free end of the connector, wherein the alarm unit, power source, and detection system are positioned within the free end of the connector.

2. The endoscope assembly as claimed in claim 1 wherein the alarm unit comprises a light emitting diode.

3. The endoscope assembly as claimed in claim 1 wherein the alarm unit comprises a sound producing speaker.

4. The endoscope assembly as claimed in claim 1 wherein the power supply for powering the alarm unit comprises a high capacitance capacitor.

5. The endoscope assembly as claimed in claim 1 wherein the power supply for powering the alarm unit comprises an electrical accumulator.

6. The endoscope assembly as claimed in claim 1 wherein the power source for powering the alarm unit is charged when the connector is connected to the control unit.

7. The endoscope assembly as claimed in claim 1 wherein the detection system comprises a micro-switch for detecting the absence of the connector cover.

8. The endoscope as assembly claimed in claim 1 wherein the detection system comprises a reed contact with magnetic system for detecting the absence of the connector cover.

9. The endoscope assembly as claimed in claim 1 wherein the detection system comprises a photodiode or phototransistor for detecting the absence of the connector cover.

10. The endoscope assembly as claimed in claim 9, further comprising a comparator to compare a signal generated by the photodiode with a threshold signal to estimate a presence or the absence of said connector cover.

11. The endoscope assembly as claimed in claim 1 wherein the detection system comprises an optocoupler for detecting the absence of the connector cover.

12. An endoscope system, comprising:
- a control unit;
- an endoscope assembly;
- a connector for connecting the endoscope assembly to the control unit, the connector including a cable, wherein the cable has a fixed end on the endoscope assembly, and a free end opposite the fixed end, wherein the free end of the connector is configured to be received by the control unit to couple the endoscope assembly to the control unit, and withdrawn from the control unit;
- a connector cover adapted to cover the free end of the connector, thereby blocking receipt of the free end of the connector by the control unit;
- a detection system, positioned within said free end of the connector, to generate a signal indicative of a presence or absence of the connector cover on said free end of the connector while said free end of the connector is not received by the control unit; and
- a notification system, positioned within said free end of the connector, to receive and process said signal generated by the detection system and, based on said signal, activate or deactivate an alarm to communicate a presence or absence of said connector cover on the free end of the connector.

13. The endoscope system as claimed in claim 12 wherein said notification system comprises a microcontroller or a processing unit to analyze said signal.

14. The endoscope system as claimed in claim 12 wherein said notification system comprises at least one of a light based alarm unit or a sound based alarm unit.

15. The endoscope system as claimed in claim 12 wherein said detection system comprises at least one of a micro switch or a reed contact with a magnetic system.

16. The endoscope system as claimed in claim 12 wherein said detection system comprises a photodiode.

17. The endoscope system as claimed in claim 16, further comprising a comparator to compare a signal generated by the photodiode with a threshold signal to estimate a presence or absence of said connector cover.

18. The endoscope system as claimed in claim 12 wherein said detection system comprises an optocoupler.

19. The endoscope system as claimed in claim 12 further comprising a power source for powering said alarm unit.

20. The endoscope system as claimed in claim 19 wherein said power source is at least one of a capacitor or an electrical accumulator.

21. The endoscope system as claimed in claim 19, wherein the power source used for powering the alarm unit is adapted to be charged when said free end of the connector is connected to the control unit.

22. An endoscope system comprising:
- a connector for connecting an endoscope assembly to a main control unit of endoscope, the connector including a fixed end at the endoscope assembly, and a free end opposite the fixed end;
- a connector cover to encompass at least a portion of said free end of the connector when said free end of the connector is not connected to said main control unit, the connector cover blocking connection of the free end of the connector to the main control unit when the connector cover encompasses at least the portion of the free end of the connector;
- an alarm system, positioned within said free end of the connector, to indicate an absence of said connector cover over said free end of the connector; and
- the main control unit comprising a regulator to control said alarm system when said free end of the connector is connected with the main control unit.

23. The endoscope system as claimed in claim 22, wherein said connector cover comprises a micro switch to detect a presence of the connector cover when said free end of the connector is not connected to said main control unit.

24. The endoscope system as claimed in claim 22, wherein said connector cover comprises a reed contact with a magnetic switch to detect a presence of the connector cover when said free end of the connector is not connected to said main control unit.

25. The endoscope system as claimed in claim 24, wherein said connector cover comprises a magnet to regulate a function of said reed contact.

26. The endoscope system as claimed in claim 22, wherein said connector cover comprises a photo sensing device to detect a presence of the connector cover when said free end of the connector is not connected to said main control unit.

27. The endoscope system as claimed in claim 22, wherein said connector cover comprises an optocoupler to detect a presence of the connector cover when said free end of the connector is not connected to said main control unit.

28. The endoscope system as claimed in claim 22, wherein said alarm system comprises at least one of an acoustic indicator or a visual indicator.

29. The endoscope system as claimed in claim 22, wherein said connector comprises at least one of a power supply module to provide a power source for at least a portion of the alarm system, a charger, or a power control unit to regulate a power supply module.

30. The endoscope system as claimed in claim 29, wherein said main control unit provides power to charge said power supply module when said main control unit is connected to said free end of the connector.

* * * * *